United States Patent [19]

Lauritzen

[11] Patent Number: 4,808,738
[45] Date of Patent: Feb. 28, 1989

[54] ETHYLENE OXIDE PROCESS
[75] Inventor: Ann M. Lauritzen, Houston, Tex.
[73] Assignee: Shell Oil Company, Houston, Tex.
[21] Appl. No.: 184,531
[22] Filed: Apr. 20, 1988

Related U.S. Application Data

[62] Division of Ser. No. 926,025, Oct. 31, 1986, Pat. No. 4,766,105.

[51] Int. Cl.$^4$ ............................................. C07D 301/10
[52] U.S. Cl. ........................................................... 549/536
[58] Field of Search ............................................ 549/536

[56] References Cited

U.S. PATENT DOCUMENTS

| | | | |
|---|---|---|---|
| 3,316,279 | 4/1967 | Fenton | 260/348.5 |
| 3,449,078 | 6/1969 | Quik et al. | 23/212 |
| 3,702,259 | 11/1972 | Nielsen | 117/37 R |
| 3,844,981 | 10/1974 | Cusumano | 252/471 |
| 3,962,136 | 6/1976 | Nielsen et al. | 252/454 |
| 3,962,285 | 6/1976 | Cusumano | 260/348.5 R |
| 3,972,829 | 8/1976 | Michalko | 252/430 |
| 4,005,049 | 1/1977 | Fields | 252/467 |
| 4,010,115 | 3/1977 | Nielsen et al. | 252/454 |
| 4,012,425 | 3/1977 | Nielsen et al. | 260/348.5 R |
| 4,242,235 | 12/1980 | Cognion | 252/455 R |
| 4,341,664 | 7/1982 | Antos | 252/466 PT |
| 4,342,667 | 8/1982 | Armstrong et al. | 252/476 |
| 4,350,616 | 9/1982 | Boussert | 252/463 |
| 4,356,312 | 10/1982 | Nielsen et al. | 549/534 |
| 4,459,372 | 1/1984 | Arema | 502/351 |
| 4,536,482 | 8/1985 | Carcia | 502/5 |
| 4,548,921 | 10/1985 | Geus et al. | 502/330 |

FOREIGN PATENT DOCUMENTS 0172565  2/1986  European Pat. Off.
1325715  8/1973  United Kingdom.

*Primary Examiner*—W. J. Shine

[57] ABSTRACT

This invention relates to an ethylene oxide catalyst having an improved selectivity which catalyst comprises silver, a promoting amount of alkali metal, a promoting amount of rhenium and a promoting amount of rhenium co-promoter selected from sulfur, molybdenum, tungsten, chromium and mixtures thereof supported on a porous refractory support.

125 Claims, 4 Drawing Sheets

ETHYLENE OXIDE PROCESS

This is a division of application Ser. No. 926,025 filed Oct. 31, 1986, now U.S. Pat. No. 4,766,105.

FIELD OF THE INVENTION

This invention relates to supported silver-based catalysts for the production of ethylene oxide.

BACKGROUND OF THE INVENTION

Supported silver catalysts have long been used in the conversion of ethylene and oxygen to ethylene oxide. The use of small amounts of the alkali metals, K, Rb and Cs, were noted as useful promoters in supported silver catalysts in U.S. Pat. Nos. 3,962,136, issued June 8, 1976 and 4,010,115, issued Mar. 1, 1977.

U.S. Pat. No. 3,844,981 issued Oct. 29, 1974, U.S. Pat. No. 3,962,285 issued June 8, 1976 and British Pat. No. 1,325,715, published Aug. 8, 1973, disclose the use of silver-rhenium ethylene oxide catalysts. In these patents a high surface area silver derivative such as silver oxide is impregnated with a rhenium solution and subsequently reduced to provide metallic rhenium alloyed with the silver. The '285 patent discloses the use of KOH to precipitate $Ag_2O$ from $AgNO_3$. There is no disclosure in the patents of the use of suitable inert supports such as porous refractory supports. U.S. Pat. No. 4,584,921, issued Oct. 22, 1985, discloses the use of rhenium in silver-supported ethylene oxide catalysts. In this reference, the rhenium is first placed on the support in the form of finely divided metal particles and the silver is subsequently deposited on the outer surface of the particles. U.S. Pat. No. 3,316,279, issued Apr. 25, 1967, discloses the use of rhenium compounds, particularly ammonium and alkali metal perrhenate for the oxidation of olefins to olefin oxides. In this reference, however, the rhenium compounds are used, unsupported along with a reaction modifier (cyanides, pyridines or quinolines) in a liquid phase reaction. U.S. Pat. No. 3,972,829, issued Aug. 3, 1976, discloses a method for distributing catalytically active metallic components on supports using an impregnating solution of catalyst precursor compound and an organic thioacid or a mercaptocarboxylic acid. Catalytically active metals include metals of Groups IVA, IB, VIB, VIIB and VIII, including rhenium and which may be in either the oxidized or reduced state. However, promoting amounts of rhenium in combination with silver and promoter amounts of alkali metal on a porous refractory support are not suggested. U.S. Pat. No. 4,459,372, issued July 10, 1984, discloses the use of rhenium metal in combination with a surface metallated (using Ti, Zr, Hf, V, Sb, Pb, Ta, Nb, Ge and/or Si) alumina or silica. U.S. Pat. No. 4,005,049, issued Jan. 25, 1977, teaches the preparation of a silver/transition metal catalyst useful in oxidation reactions. In this instance, the silver serves as both a catalyst and a support for the transition metal co-catalyst. In U.S. Pat. No. 4,536,482, issued Aug. 20, 1985, catalytically active metals such as Ag and Re are co-sputtered along with a co-sputtered support material on a particular support. None of these references disclose the use of a promoting amount of rhenium which is present on a silver-based, alkali-doped supported catalyst.

SUMMARY OF THE INVENTION

This invention relates to a catalyst for the production of ethylene oxide from ethylene and molecular oxygen in the vapor phase which catalyst comprises a catalytically effective amount of silver, a promoting amount of alkali metal, a promoting amount of rhenium and a promoting amount of a rhenium co-promoter selected from sulfur, molybdenum, tungsten, chromium and mixtures thereof supported on a porous, refractory support. In a preferred embodiment the alkali metal is a higher alkali metal of potassium, rubidium, cesium or mixtures thereof and is present in an amount ranging from about 20 to about 1500 ppm by weight of the total catalyst, the rhenium is present in an amount ranging from about 0.2 to about 5 millimoles of rhenium per kilogram of total catalyst and the rhenium co-promoter is present in an amount ranging from about 0.2 to about 5 millimoles, measured as the element per kilogram of total catalyst. The rhenium may conveniently be a form of rhenium which is extractable in a dilute aqueous alkali metal hydroxide solution, particularly a 20 millimolar sodium hydroxide solution. In a preferred embodiment the instant combination of silver, alkali metal promoter, rhenium and rhenium co-promoter on the support affords higher selectivities, particularly higher initial selectivities to ethylene oxide at a given oxygen conversion level than is obtained under the same reaction conditions with the same combination of silver and support and none, one or two of the promoters selected from alkali metal, rhenium and rhenium co-promoter.

DETAILED DESCRIPTION OF THE INVENTION

Figure 1:
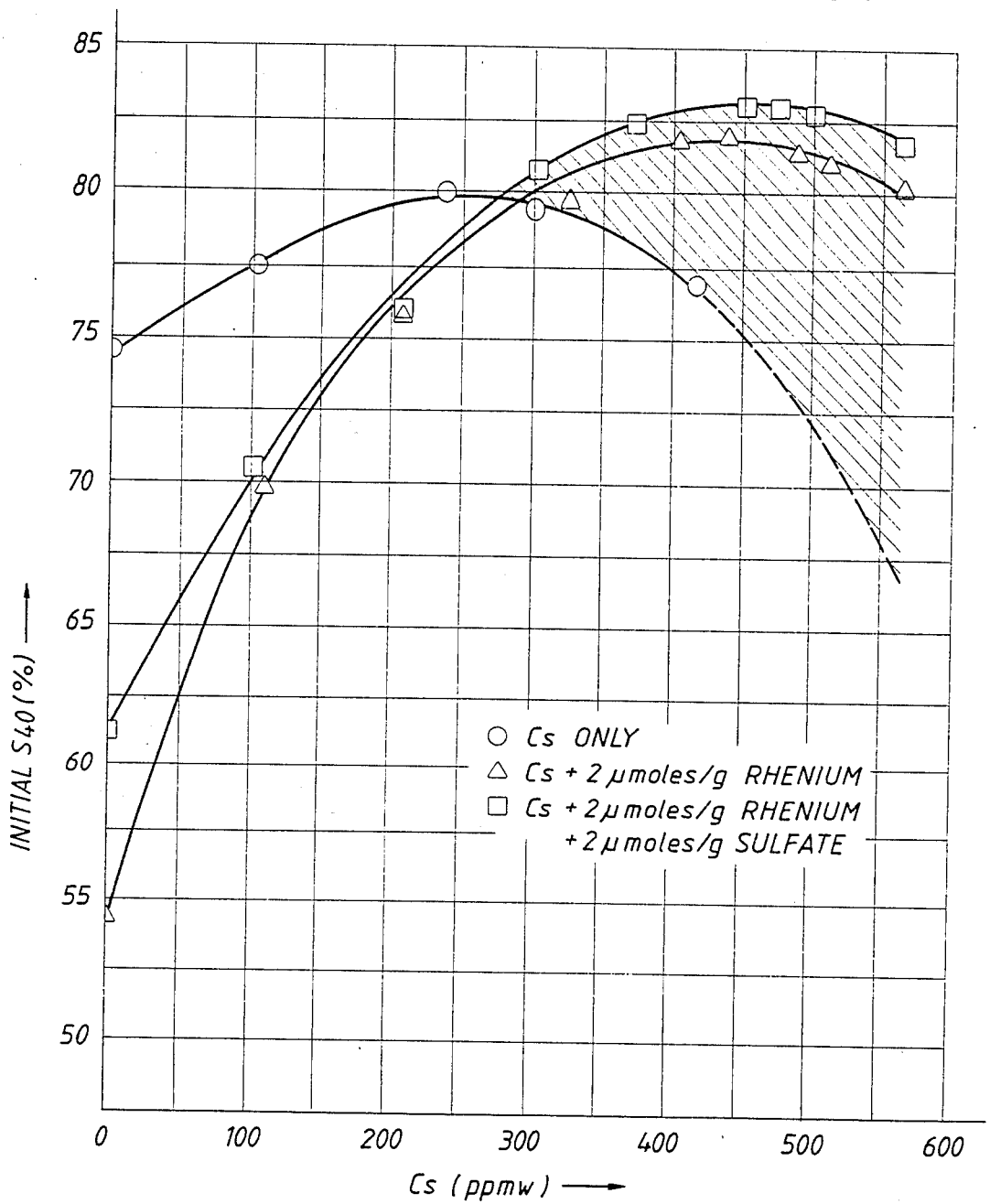
FIG. 1 shows optimized initial selectivity versus cesium promoter concentration for a catalyst of the instant invention containing rhenium and rhenium co-promoter, for a catalyst containing rhenium and for a catalyst not containing rhenium and rhenium co-promoter thereby illustrating the enhanced initial selectivity obtained with the instant catalyst.
Figure 2:
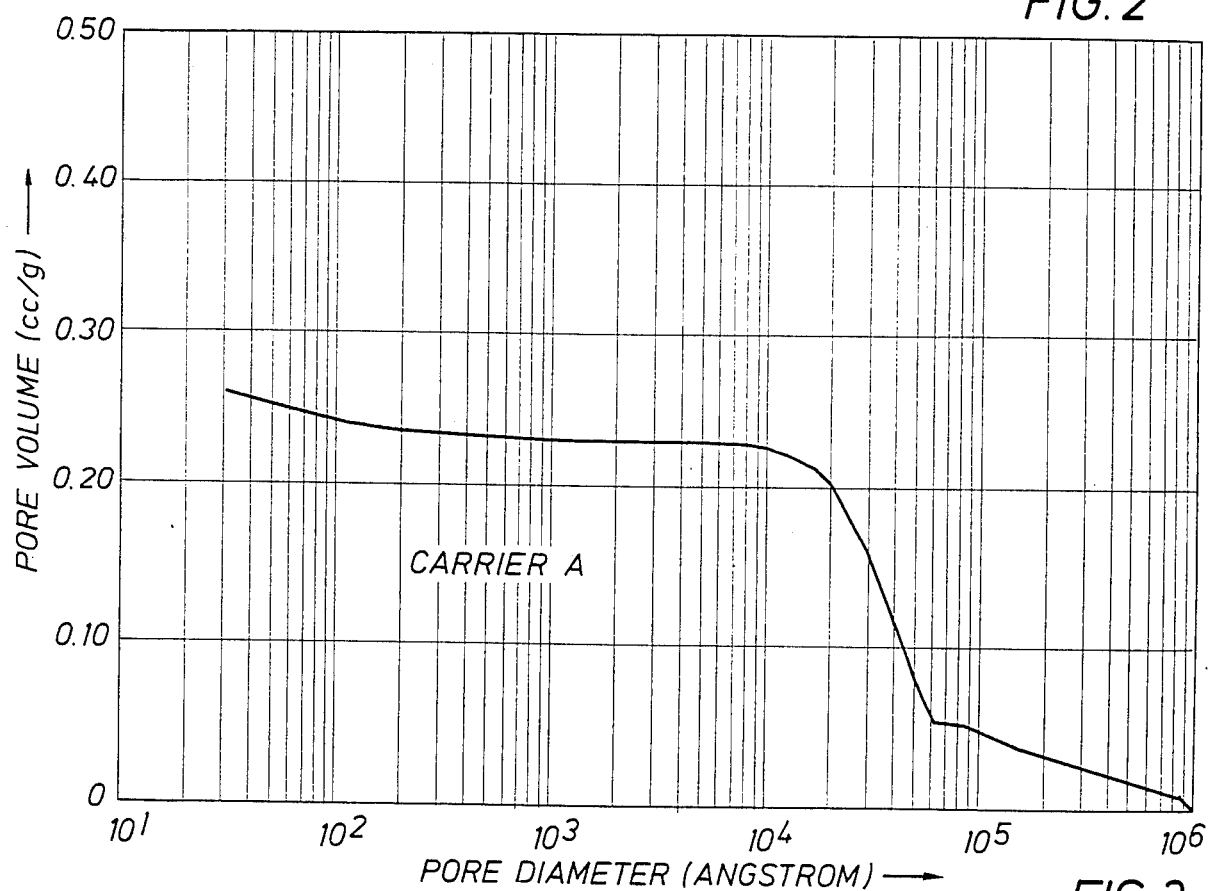
FIGS. 2-7 show pore size distribution curves for carriers A-F of Table 1.
Figure 3:
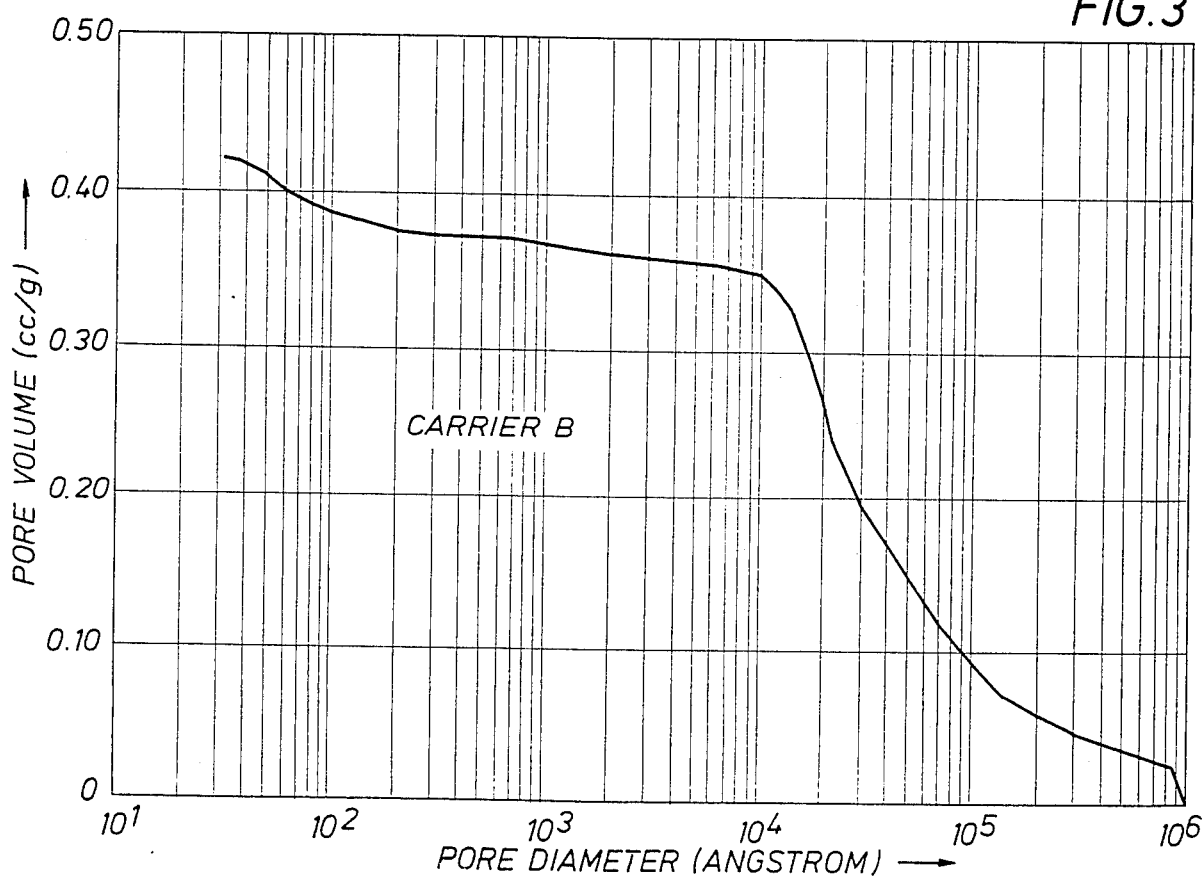
Figure 4:
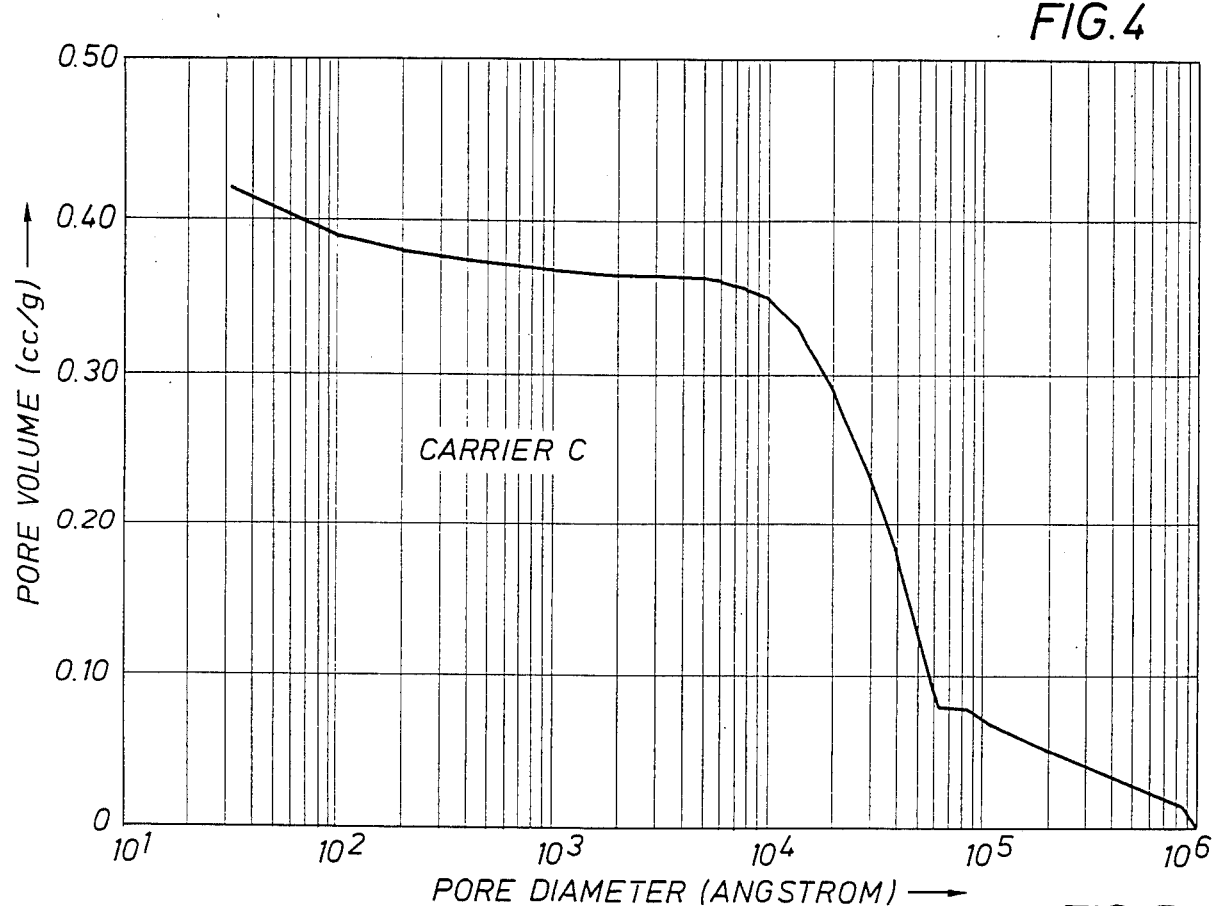
Figure 5:
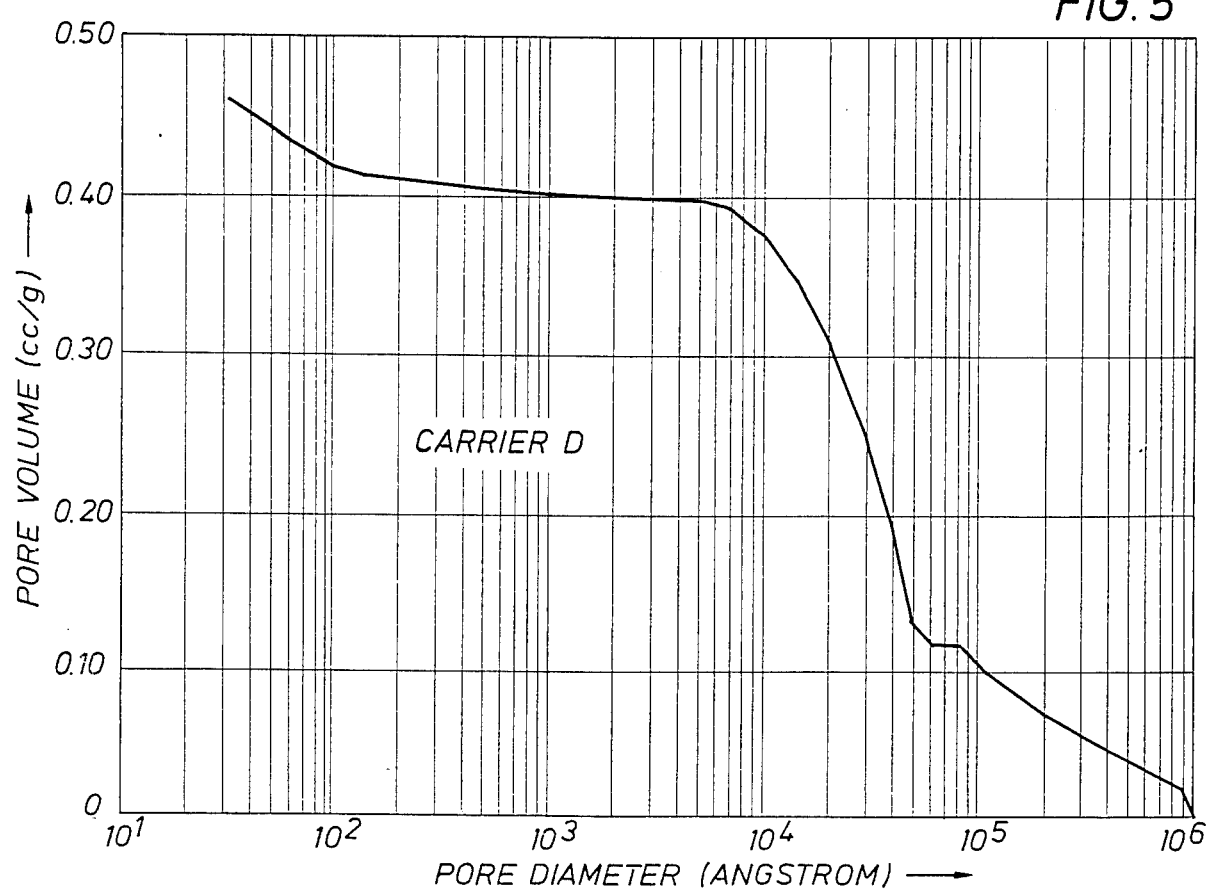
Figure 6:
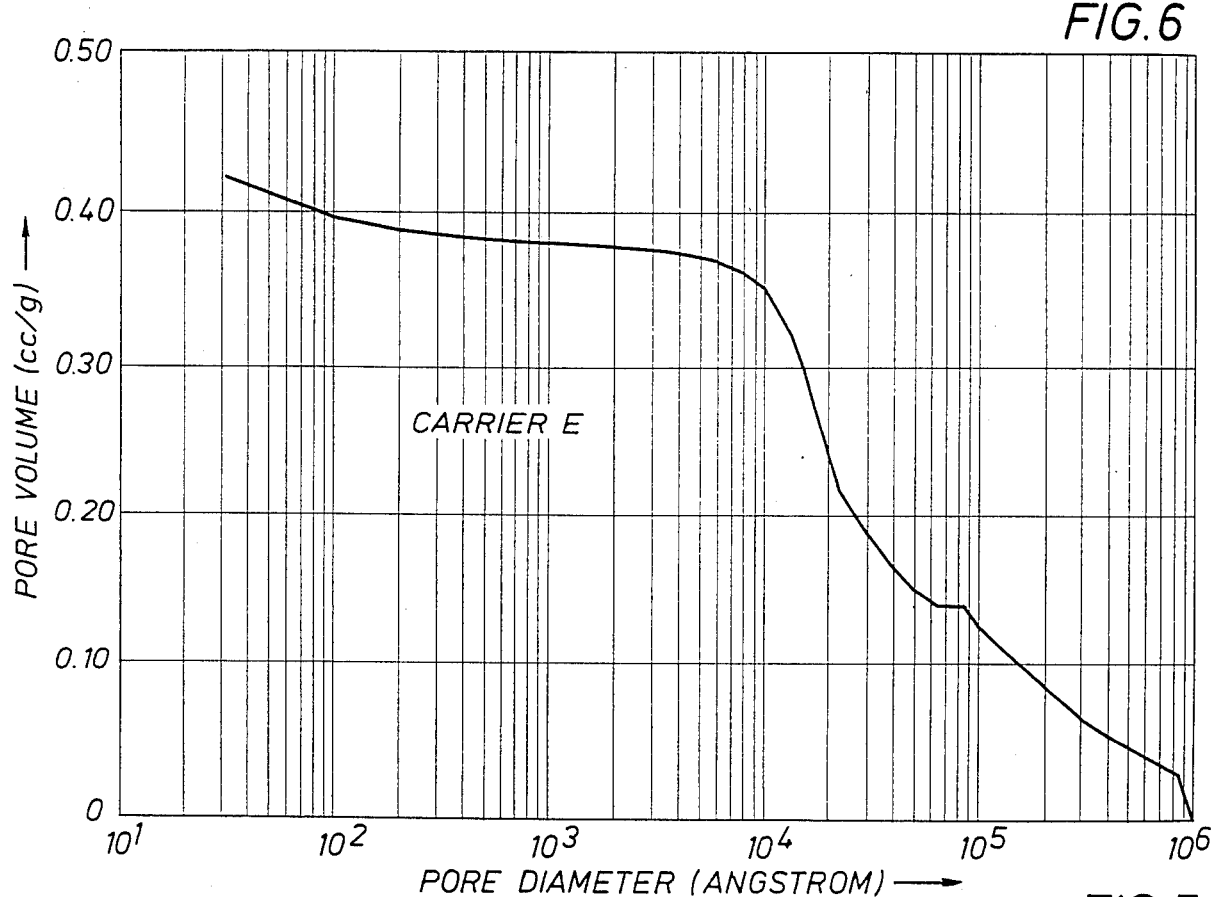
Figure 7:
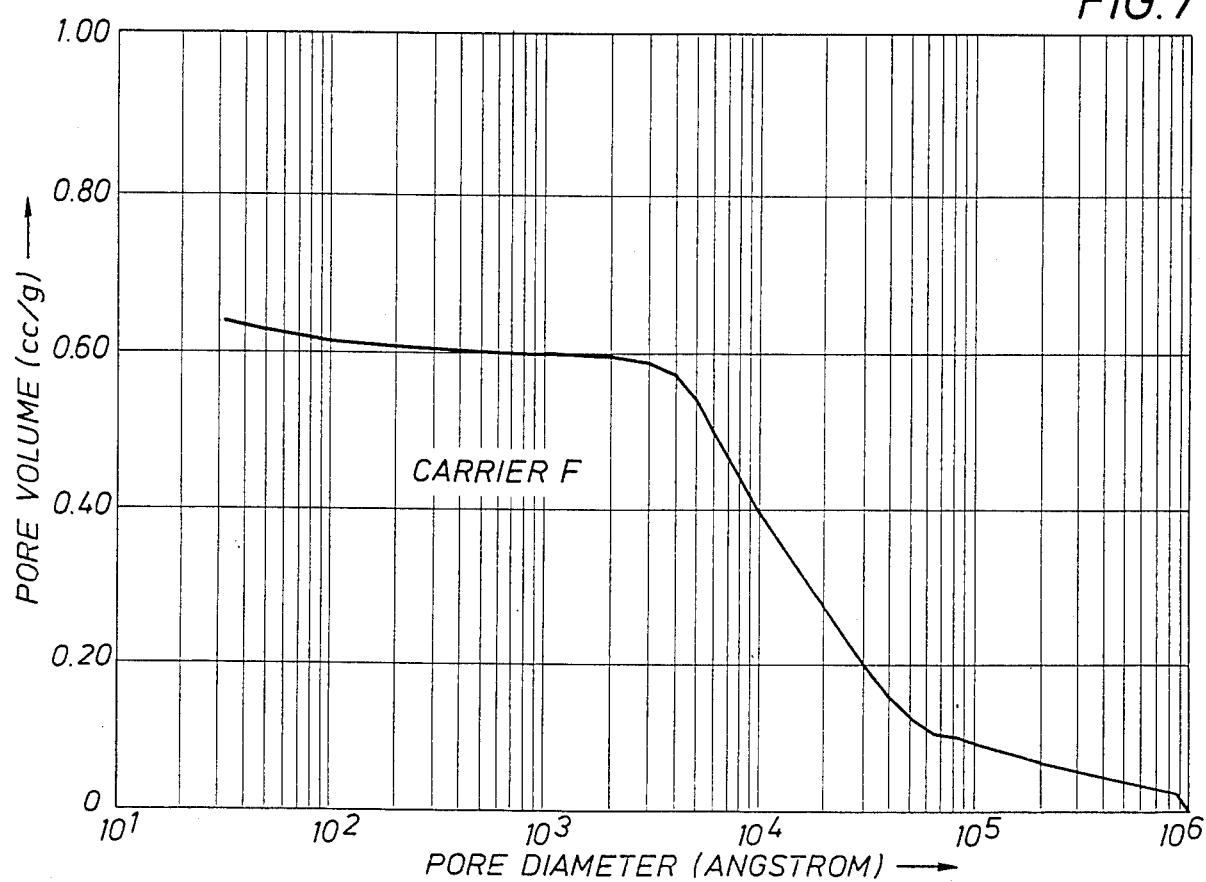

Generally, in the vapor phase reaction of ethylene with oxygen to produce ethylene oxide, the ethylene is present in at least a double amount (on a mol basis) compared with oxygen, but frequently is often much higher. Therefore the conversion is calculated according to the mol percentage of oxygen which has been used in the reaction. The oxygen conversion is dependent on the reaction temperature which latter is a measure of the activity of the catalyst employed. The value $T_{40}$ indicates the temperature at 40 mol percent conversion of the oxygen in the reactor and the value T is expressed in °C. This temperature is higher when the conversion of oxygen is higher. Moreover this temperature is strongly dependent on the employed catalyst and the reaction conditions. The selectivity (to ethylene oxide) indicates the molar amount of ethylene oxide in the reaction product compared with the total molar amount of ethylene converted. Herein the selectivity is indicated as $S_{40}$, which means the selectivity at 40 mol percent oxygen conversion. The selectivity of silver-based ethylene oxide catalysts can decrease over a period of time of usage. When comparing the selectivity performance of various silver-based ethylene oxide catalysts, it is important that the selectivity value be measured at approximately the same period of time of usage under the same or similar reaction conditions. As used herein, "initial selectivity" will refer to the selectivity of ethylene oxide catalysts when measured at a given constant oxygen conversion level of 40% at a gas hourly space velocity of approximately 3300 and when measured after the catalyst has been placed on stream for about 16±4 hours. Unless otherwise noted, all selectivities that are provided in the examples provided herein are initial selectivities.

In broad general terms the catalysts of the instant invention are prepared by impregnating porous refractory supports with silver ions or compound(s), complex(es) and/or salt(s) dissolved in a suitable solvent sufficient to cause deposition on the support of from about 1 to about 25 percent by weight, basis total catalyst, of silver; the thus impregnated carrier is then separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Also deposited on the carrier either prior to, coincidentally with, or subsequent to the deposition of the silver and/or alkali metal will be suitable rhenium ion(s) or compound(s), complex(es) and/or salt(s) dissolved in an appropriate solvent. Also deposited on the carrier prior to, coincidentally with, or subsequent to the deposition of the silver and/or alkali metal and/or rhenium will be suitable ions or salt(s), complex(es) and/or compound(s) of sulfur, molybdenum, tungsten and/or chromium dissolved in an appropriate solvent. Detailed preparative techniques are discussed herein.

The support or carrier employed in these catalysts in its broadest aspects is selected from the larger number of conventional, porous refractory catalyst carriers or support materials which are considered relatively inert in the presence of the ethylene oxidation feeds, products and reaction conditions. Such conventional materials are known to persons skilled in the art and may be of natural or synthetic origin and preferably are of a macroporous structure, that is, a structure having a surface area below about 10 $m^2/g$ and preferably below about 3 $m^2/g$. Very suitable supports comprise those of aluminous composition. Examples of supports that have been used as supports for different catalysts and which could, it is believed, be used as supports for ethylene oxide catalysts are the aluminum oxides (including the materials sold under the trade name "Alundum"), charcoal, pumice, magnesia, zirconia, keiselguhr, fullers' earth, silicon carbide, porous agglomerates comprising silica and/or silicon carbide, silica, magnesia, selected clays, artificial and natural zeolites and ceramics. Refractory supports particularly useful in the preparation of catalysts in accordance with this invention comprise the aluminous materials, in particular those comprising alpha alumina. In the case of alpha alumina-containing supports, preference is given to those having a specific surface area as measured by the B.E.T. method of from about 0.03 $m^2/g$ to about 10 $m^2/g$, preferably from about 0.05 to about 5, more preferably from about 0.1 to about 3 $m^2/g$, and a water pore volume as measured by conventional water absorption techniques of from about 0.1 to about 0.75 cc/g by volume. The B.E.T. method for determining specific surface area is described in detail in Brunauer, S., Emmett, P.H. and Teller, E., *J. Am. Chem. Soc.*, 60, 309–16 (1938).

Certain types of alpha alumina-containing supports are particularly preferred. These alpha alumina supports have relatively uniform pore diameters and are more fully characterized by having (1) B.E.T. specific surface areas of from about 0.1 $m^2/g$ to about 3.0 $m^2/g$, preferably about 0.1 $m^2/g$ to about 2.0 $m^2/g$ and (2) water pore volumes of from about 0.10 cc/g to about 0.75 cc/g, preferably from about 0.25 cc/g to about 0.55 cc/g. Typical properties of some supports found particularly useful in the instant invention are shown in Table 1. Suitable manufacturers of carriers comparable to those in Table 1 include Norton Company and United Catalysts, Inc. (UCI).

TABLE 1

| Carrier | A | B | C | D | E | F |
|---|---|---|---|---|---|---|
| B.E.T. Surface Area, $m^2/g^{(a)}$ | 0.21 | 0.42 | 0.42 | 0.48 | 0.57 | 2.06 |
| Water Pore Volume, cc/g | 0.26 | 0.36 | 0.41 | 0.49 | 0.44 | 0.65 |
| Crush Strength, FPCS, lbs[b] | 100% 20 lbs | 97% 15 | Avg 21 Range 15–30 | 90% 14 | 90% 15 | No Data |
| Total Pore Volume, Hg, cc/g[c] | 0.26 | 0.42 | 0.42 | 0.46 | 0.42 | 0.65 |
| Average Pore Diameter, Hg, Å[c] | 620 | 560 | 640 | 550 | 770 | 1000 |
| Median Pore Diameter, Hg, microns[c,e] | 3.7 | 2.7 | 3.4 | 3.4 | 2.4 | 2.5 |
| Percent Pore Volume in Pores Greater Than 350 Å[c] | 90.0% | 88.5% | 89.5% | 89.1% | 91.5% | 94.1% |
| Percent Pore Volume in Pores Greater Than 1 Micron[c] | 87.0% | 82.5% | 83.4% | 82.3% | 83.5% | 61.0% |
| % Wt. Alpha Alumina | 99.5 | 98 | 98.5 | 98.5 | 98 | 70–75 |
| Water Leachable Na, ppmw | 12 | 53 | 21 | 24 | 18 | No Data |
| Acid-Leachable Na, ppmw | 40 | 96 | 87 | 51 | 45 | No Data |
| Water-Leachable K, ppmw | 5 | 22 | 21 | 22 | 10 | No Data |
| Acid-Leachable Fe, ppmw | 2 | 5 | No Data | 1 | 5 | No Data |

TABLE 1-continued

| Carrier | A | B | C | D | E | F |
|---|---|---|---|---|---|---|
| % Wt. SiO$_2$ | .5 | 2 | 1.5 | 15 | 2 | 25–30 |

(a) Method of Brunauer, Emmett and Teller, loc. cit.
(b) Flat Plate Crush Strength, single pellet.
(c) Determined by mercury intrusion to 55,000 psia using Micrometrics Autopore 9200 or 9210 (130° Contact angle, 0.473 N/m surface tension of Hg).
(e) Median pore diameter represents the pore diameter wherein 50% of the total pore volume is found in pores having less than (or greater than) the median pore diameter.

Pore size distribution curves measured by mercury intrusion techniques noted in footnote (c) above in Table 1 for carriers A–F are shown in FIGS. 2–7.

Of the carriers listed in Table 1, B & D are preferred because they provide catalysts which show better overall initial performance in terms of initial selectivity and initial activity.

Regardless of the character of the support or carrier used, it is preferably shaped into particles, chunks, pieces, pellets, rings, spheres, wagon wheels, and the like of a size suitable for employment in fixed bed reactors. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15–45 feet long filled with catalyst. In such reactors, it is desirable to employ a support formed into a rounded shape, such as for example, spheres, pellets, rings, tablets and the like, having diameters from about 0.1 inch to about 0.8 inch.

Particular supports may be selected having differing properties such as surface area and pore volume in order to provide particular catalytic properties. With regard to surface area (B.E.T.) possible lower limits are, for example, about 0.01, 0.03, 0.05, 0.75, 0.1, 0.15 and 0.2 m$^2$/g and possible upper limits are, for example, about 0.6, 0.75, 0.9, 1, 2, 2.5, 3, 4, 5 and 10 m$^2$/g. With regard to water pore volume, possible lower limits are, for example, about 0.05, 0.1 0.15, 0.2 and 0.35 cc/g and possible upper limits are, for example, about 0.5, 0.55, 0.6, 0.65, 0.7, 0.75 and 0.8 cc/g.

The catalysts of the instant invention are prepared by a technique in which the alkali metal promoters, the rhenium and the rhenium co-promoter in the form of soluble salts and/or compounds are deposited on the catalyst and/or support prior to, simultaneously with, or subsequent to the deposition of the silver and each other. The alkali metals may be deposited at one step of the process and the rhenium and/or the rhenium co-promoter at a different step or steps. The preferred method is to deposit silver, alkali metal, rhenium and rhenium co-promoter simultaneously on the support, that is, in a single impregnation step, although it is believed that the individual or concurrent deposition of the alkali metal, rhenium and rhenium co-promoters prior to and/or subsequent to the deposition of the silver produces suitable silver catalysts.

Promoting amounts of alkali metal or mixtures of alkali metal are deposited on a porous support using a suitable solution. Although alkali metals exist in a pure metallic state, they are not in that form suitable for use. They are utilized as ions or salts or compounds of alkali metals dissolved in a suitable solvent for impregnation purposes. The carrier is impregnated with a solution of alkali metal promoter ions, salt(s) and/or compound(s) before, during or after impregnation or deposition of the silver ions or salt(s), complex(es), and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, silver content of the catalyst and the particular ions used in conjunction with the alkali metal cation or rhenium or rhenium co-promoter and amounts of rhenium and rhenium co-promoter present. The amount of alkali metal promoter deposited upon the support or present on the catalyst generally lies between about 10 and about 3000, preferably between about 15 and about 2000 and more preferably between about 20 and about 1500 parts by weight per million parts by weight of total catalyst. Most preferably, the amounts range between about 50 and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions such as ions added with the alkali metal, rhenium, or rhenium co-promoter or compounds remaining from the impregnating solution and the above-defined limits were selected to cover the widest possible variations in properties and characteristics. The effects of these variations are readily determined by experimentation. The alkali metal promoters are present on the catalysts in the form of cations (ions) or compounds or complexes or surface compounds or surface complexes rather than as the extremely active free alkali metals, although for convenience purposes in this specification and claims they are referred to as "alkali metal" or "alkali metal promoters" even though not present on the catalyst as metals. For purposes of convenience the amount of alkali metal deposited on the support or present on the catalyst is measured as the metal rather than in the cationic or compound form. Thus, the alkali metal promoters are present on the support or catalyst in the form of cations (ions) or compounds or complexes or surface compounds or surface complexes. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture such as chlorides or carbonates or residual species from the impregnation solution(s).

In a preferred embodiment, at least a major proportion (greater than 50%) of the alkali metals are selected from the group consisting of potassium, rubidium, cesium and mixtures thereof.

In this preferred embodiment, the alkali metals comprise the higher alkali metals. As used the term "higher alkali metal" and cognates thereof refers to the alkali metals selected from the group consisting of potassium, rubidium, cesium and mixtures thereof. As used herein, the term "mixtures of alkali metals" or "mixtures of higher alkali metals" or cognates of these terms refers to the use of two or more of the alkali or higher alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. When the alkali metal comprises mixtures of higher alkali metals, at least two of the following are used: potassium, rubidium or cesium. Thus, for example, in the preferred embodiment wherein the higher alkali metal comprises potassium, rubidium, cesium or mixtures thereof, potassium may be used with cesium, or rubidium may be used with cesium, or potassium may be used with rubidium or all three may be used together. Hence, for example, when potassium is used with cesium, the weight percent ratio of potassium to cesium will range from 0/100 to 100/0, including all ranges in between such as 20/80, 50/50, 75/25 etc. and similar relationships will apply to other mixtures. A particularly preferred alkali metal promoter is cesium.

It must be clear that the amounts of alkali metal promoters on the catalysts are not necessarily the total amounts of these metals present in the catalyst. They are amounts that have been added to the catalyst by impregnation with a suitable solution of ions, salts and/or compounds and/or complexes of alkali metals. These amounts do not include amounts of alkali metals that are locked into the support, say by calcining, or are not extractable in a suitable solvent such as water or lower alkanol or amine or mixtures thereof and do not provide a promoting effect. It is also understood that the source of the alkali metal promoter ions, salts and/or compounds used to impregnate the catalyst may be the carrier. That is, the carrier may contain extractable amounts of alkali metal that can be extracted with a suitable solvent, such as water or lower alkanol thus preparing an impregnating solution from which the alkali metal ions, salts and/or compounds are deposited or redeposited on the support.

As used herein, the term "compound" refers to the combination of a particular element with one or more different elements by surface and/or chemical bonding, such as ionic and/or covalent and/or coordinate bonding. The term "ionic" or "ion" refers to an electrically chemical charged moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge balancing counter ions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, by way of nonlimiting example, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As used herein the term "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will internationally change the operating conditions in order to take advantage of certain catalytic properties even at the expense of other catalytic properties in order to maximize profits by taking into account feedstock costs, energy costs, by-product removal costs and the like. The particular combination of silver, support, alkali metal promoter, rhenium promoter and rhenium co-promoter of the instant invention will provide an improvement in one or more catalytic properties over the same combination of silver and support and none, one or two of the promoters selected from alkali metal, rhenium and rhenium co-promoter; that is, no promoters; alkali metal as the only promoter; rhenium as the only promoter; rhenium co-promoter as the only promoter; alkali metal and rhenium as promoters; alkali metal and rhenium co-promoter as promoters; and rhenium and rhenium co-promoter as promoters.

As used herein, the term "catalytically effective amount of silver" refers to an amount of silver that provides a measurable conversion of ethylene and oxygen to ethylene oxide.

The carrier is also impregnated with rhenium ions, salt(s), compound(s) and/or complex(es). This may be done at the same time that the alkali metal promoter is added, before or later; or at the same time that the silver is added or before or later; or at the same time that the rhenium co-promoter is added or before or later. Preferably, rhenium, rhenium co-promoter, alkali metal and silver are in the same impregnating solution, although it is believed that their presence in different solutions will still provide suitable catalysts. The preferred amount of rhenium, calculated as the metal, deposited on or present on the carrier or catalyst ranges from about 0.1 mmoles to about 10 mmoles, more preferably from about 0.2 mmoles to about 5 mmoles per kilogram of total catalyst, or alternatively stated from about 19 to about 1860, more preferably from about 37 to about 930 parts by weight per million parts by weight of total catalyst. The degree of benefit obtained within the above-defined limits will vary depending upon particular properties and characteristics, such as, for example, reaction conditions, catalyst preparative conditions, surface area and pore structure and surface chemical properties of the carrier utilized, silver content of the catalyst and other compounds, anions or cations present besides those containing rhenium, alkali metal or rhenium co-promoter, such as ions added with the alkali metal, rhenium or rhenium co-promoter, or compounds remaining from the impregnating technique, and the above-defined limits were selected to cover the widest possible variations in properties and characteristics. The effects of these variations are readily determined by experimentation. For purposes of convenience, the amount of rhenium present on the catalyst is measured as the metal, irrespective of the form in which it is present.

The promoting effect provided by the rhenium can be affected by a number of variables such as for example, reaction conditions, catalyst preparative techniques, surface area and pore structure and surface chemical properties of the support, the silver and alkali metal and rhenium co-promoter content of the catalyst, the presence of other cations and anions present on the catalyst alone or in combination with the alkali metal and/or rhenium and/or rhenium co-promoter. The presence of other activators, stabilizers, promoters, enhancers or other catalyst improvers can also affect the promoting effects of the rhenium. It is understood that any supported silver-based, alkali metal promoted ethylene oxide catalyst which contains other cations and/or anions or any other activators, promoters, enhancers, stabilizers or other catalyst improvers and which contains an amount of rhenium and rhenium co-promoter which proves a promoting effect, more preferably which provides higher ethylene oxidation selectivities to ethylene oxide at a given oxygen conversion level and most preferably which provides higher initial ethylene oxidation selectivities than is obtained under the same reaction conditions with the same catalyst which contains none, one or two of the promoters selected from alkali metal, rhenium and rhenium co-promoter will fall within the scope of the instant invention and claims.

The rhenium compounds used in the preparation of the instant catalysts are rhenium compounds that can be solubilzed in an appropriate solvent. Preferably the solvent is a water-containing solvent. More preferably the solvent is the same solvent used to deposit the silver and the alkali metal promoter. Examples of rhenium compounds include the rhenium salts such as rhenium halides, the rhenium oxyhalides, the rhenates, the perrhenates, the oxides and the acids of rhenium. A preferred compound to be utilized in the impregnation solution is the perrhenate, preferably ammonium perrhenate. However, the alkali metal perrhenates, alkaline earth metal perrhenates, silver perrhenate, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4^-$. It is also understood that there are many rhenium compounds that are not soluble per se in water. However, these compounds can be solubilized by utilizing various acids, bases, peroxides, alcohols, etc. After solubilization these compounds could be used, for example, with an appropriate amount of water or other suitable solvent to impregnate the carriers. Of course, it is also understood that upon solubilization of many of these compounds, the original compound no longer exists after solubilization. For example, rhenium metal is not soluble in water. However, it is soluble in concentrated nitric acid as well as in hydrogen peroxide solution. Thus, by using an appropriate reactive solvent one could use rhenium metal to prepare a solubilized rhenium-containing impregnating solution.

A presently preferred aspect of the instant invention is that the rhenium present on the catalyst is present in a form that is extractable in a dilute aqueous base solution. For the purposes of this specification a 20 millimolar aqueous sodium hydroxide solution was chosen as the standard solution to be used to test the extractability of rhenium on the catalyst. It will be clear to one skilled in the art that other concentrations of sodium hydroxide as well as other bases can be utilized to test the extractability of rhenium. Thus, one skilled in the art can utilize other bases, for example, other alkali metal hydroxides, other alkaline earth metal hydroxides, ammonium hydroxide, organic bases, etc., suitably dissolved in an appropriate solvent to extract rhenium and by comparing it with the 20 millimolar aqueous sodium hydroxide solution used herein can determine whether rhenium extractability with other base solutions will be equivalent to the rhenium extractability with the 20 millimolar sodium hydroxide solution.

In the above noted presently preferred embodiment, the rhenium is not present in the free metallic state, but rather is present as a compound, complex or ion. In a particularly preferred embodiment, the rhenium on the catalyst or support is in a form that is extractable by dilute basic solution, and particularly with the 20 millimolar dilute sodium hydroxide solution disclosed herein. The base extraction technique can be used on a fresh catalyst, i.e., a catalyst that has gone through all the appropriate preparative techniques and is ready to be placed in an ethylene oxide reactor, or on a used catalyst, i.e., a catalyst that has been used for the production of ethylene oxide and then removed from the reactor. In a typical test procedure utilized herein a 1 to 10 g sample of fresh or reactor-tested catalyst is extracted with 10 to 50 milliters of the 20 millimolar aqueous sodium hydroxide solution at 100° C. for 10 minutes. The amount of rhenium in an aliquot of the cooled extract is determined spectrophotometrically following the procedure of V.W. Meloche et al., *Analytical Chemistry*, 29, 527 (1957). In this procedure, a colored rhenium complex with alpha-furildioxime is formed by reduction of the rhenium species with tin (II) chloride in a dilute hydrochloric acid solution containing a large excess of alpha-furildioxime.

It has been found in co-pending Application Ser. No. 926,026, filed Oct. 31, 1986, now U.S. Pat. No. 4,761,394, that the addition of a promoting amount of rhenium to alkali metal doped supported silver catalysts improves their initial selectivity. It has now been found that if a co-promoter is added to the catalyst along with the rhenium, an even larger improvement in initial selectivity is obtained, This co-promoter is a selected from the group consisting of sulfur, molybdenum, tungsten, chromium and mixtures thereof, preferably a compound of sulfur, molybdenum, tungsten, chromium and mixtures thereof. The exact form of the co-promoter on the catalyst is not know. The co-promoter, it is believed, is not present on the catalyst in the element form since the co-promoter is applied to the catalyst in the form of ions, salts, compounds and/or complexes and the reducing conditions generally used to reduce the silver to metallic silver are not usually sufficient to reduce the sulfur, molybdenum, tungsten or chromium to the elemental form. It is believed that the co-promoter deposited on the support or present on the catalyst is in the compound form, most probably in the form of an oxygen-containing or oxidic compound. In a presently preferred embodiment, the co-promoter is applied to the catalyst in the oxyanionic form, i.e., in the form of an anion, or negative ion which contains oxygen. Examples of anions or sulfur that can be suitably applied include sulfate, sulfite, bisulfite, bisulfate, sulfonate, persulfate, thiosulfate, dithionate, dithionite, etc. Preferred compounds to be applied are ammonium sulfate and the alkali metal sulfates. Examples of anions of molybdenum, tungsten and chromium that can be suitably applied include molybdate, dimolybdate, paramolybdate, other iso- and hetero-polymolybdates, etc.; tungstate, paratungstate, metatungstate, other iso- and hetero-polytungstates, etc.; and chromate, dichromate, chromite, halochromate, etc. Preferred are sulfates, molybdates, tungstates and chromates. The anoins can be supplied with various counter-ions. Preferred are ammonium, alkali metal and hydrogen (i.e. acid form). The anions can be prepared by the reactive dissolution of various non-anionic materials such as the oxides such as $SO_2$, $SO_3$, $MoO_3$, $WO_3$, $Cr_2O_3$, as well as other materials such as halides, oxyhalides, hydroxyhalides, hydroxides, sulfides, etc., of the metals.

The carrier is impregnated with rhenium co-promoter ions, salt(s), compound(s) and/or complex(es). This may be done at the same time that the other components are added or before and/or later. Preferably rhenium co-promoter, rhenium, alkali metal and silver are in the same impregnating solution, although it is believed that their presence in different solutions will still provide suitable catalysts.

The preferred amount of co-promoter compound present on or deposited on the support or catalyst ranges from about 0.1 to about 10 mmoles, preferably from about 0.2 to about 5 millimoles, measured as the element, per kilogram of total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, alkali content of the catalyst, rhenium content of the catalyst, and other compounds, anions or cations present besides those containing rhenium, rhenium co-promoter and alkali metal, such as ions added with the alkali metal, rhenium or rhenium co-promoter, or compounds remaining from the impregnation technique, and the above-defined limits were selected to cover the widest possible variations in properties and characteristics. These variations are readily determined by experimentation. For purposes of convenience the amount of co-promoter present on the catalyst is measured as the element irrespective of the form in which it is present.

The presence of the indicated and claimed promoting amount of rhenium co-promoters in this specification and claims does not preclude the use of other activators, promoters, enhancers, stabilizers, improvers, etc., and it is not intended by the use of Markush terminology in this specification and claims to exclude the use of such other activators, promoters, enhancers, stabilizers, improvers, etc.

The co-promoter compounds, salts and/or complexes used in the preparation of the instant catalysts are compounds, salts and/or complexes that can be solubilized in an appropriate solvent. Preferably, the solvent is a water-containing solvent. More preferably the solvent is the same solvent used to deposit the silver, alkali metal promoter and rhenium. Preferred co-promoter compounds are the oxyanionic compounds of the co-promoter elements, preferably the ammonium and alkali metal oxyanionates, such as ammonium sulfate, potassium sulfate, cesium chromate, rubidium tungstate, ammonium molybdate, lithium sulfate, sodium tungstate, lithium chromate and the like.

Generally, the carrier is contacted with a silver salt, a silver compound, or a silver complex which has been dissolved in an aqueous solution, so that the carrier is impregnated with said aqueous solution; thereafter the impregnated carrier is separated from the aqueous solution, e.g., by centrifugation or filtration and then dried. The thus obtained impregnated carrier is heated to reduce the silver to metallic silver. It is conveniently heated to a temperature in the range from 50° C. to 600° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas, an inert gas or mixtures thereof may be conducted over the carrier during this heating step.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkylenediamines and ammonia. One such example of a solution of silver salts comprises an impregnating solution comprising:

A. a silver salt of a carboxylic acid,
B. an organic amine alkaline solubilizing/reducing agent, and
C. an aqueous solvent.

Suitable carboxylic acid silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are particularly useful. They are the following:

A. vicinal alkylenediamines of from 2 to 4 carbon atoms;
B. mixtures of (1) vicinal alkanolamines of from 2 to 4 carbon atoms and (2) vicinal alkylenediamines of from 2 to 4 carbon atoms;

C. mixtures of vicinal alkylenediamines of from 2 to 4 carbon atoms and ammonia; and
D. mixtures of vicinal alkanolamines of from 2 to 4 carbon atoms and ammonia. These solubilizing/reducing agents are generally added in the amount of from 0.1 to 10 moles per mole of silver present.

Particularly preferred solubilizing/reducing agents are:
A. ethylenediamine,
B. ethylenediamine in combination with ethanolamine,
C. ethylenediamine in combination with ammonia, and
D. ethanolamine in combination with ammonia.

Ethylenediamine is most preferred. Ethylenediamine in combination with ethanolamine gives comparable results, but it is believed that impurities that are present in certain commercially available ethanolamine preparations can be produce inconsistent results.

When ethylenediamine is used as the sole solubilizing/reducing agent, it is necessary to add amounts of the amine in the range of from 0.1 to 5.0 moles of ethylenediamine per mole of silver.

When ethylenediamine and ethanolamine together are used as the solubilizing/reducing agent, it is suitable to employ from 0.1 to 3.0 moles of ethylenediamine per mole of silver and from 0.1 to 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115 issued Mar. 1, 1977; and U.S. Pat. No. 4,356,312, issued Oct. 26, 1982; U.S. Pat. No. 3,962,136, issued June 8, 1976 and U.S. Pat. No. 4,012,425, issued Mar. 15, 1977, all incorporated by reference herein.

The preferred amount of alkali metal promoter deposited on or present on the surface of the carrier or catalyst generally lies between about 10 and about 3000, preferably between about 15 and about 2000 and more preferably between about 20 and about 1500 ppm by weight of alkali metal calculated on the total carrier material. Amounts between about 50 and about 1000 ppm are most preferable. Suitable compounds of alkali metal are, for example, the nitrates, carbonates, bicarbonates, oxalates, carboxylic acid salts or hydroxides put in solution, preferably aqueous solution. The most preferred promoters among the alkali metals are the alkali metals comprising the higher alkali metals comprising potassium, rubidium, cesium or mixtures thereof in a promoting amount with the even more preferred promoters being rubidium and/or cesium. Preferably the amount ranges from about 10 to about 3000, more preferably between about 15 and about 2000, even more preferably between about 20 and about 1500 ppm by weight, and most preferably between about 50 and 1000 ppm by weight. The most preferred promoter is cesium, preferably applied in an aqueous solution having cesium nitrate or cesium hydroxide dissolved therein. While the higher alkali metals provide the most significant effect when considering the selectivity, particularly the initial selectivity, it is considered within the scope of the instant preferred embodiment that lithium and/or sodium may also be present in addition to the higher alkali metal(s) in order to provide enhanced or different effects. Thus, the use of Markush terminology in this specification and claims to indicate the higher alkali metals cesium and/or rubidium and/or potassium is not meant and does not exclude the presence, inclusion or the use of lithium and/or sodium in addition to the higher alkali metals. Thus, the use of a Markush recitation in the instant specification and claim means that the elements in the recitation are included, but others are not excluded, i.e., the Markush recitation is an open ended recitation.

There are known excellent methods of applying the promoters coincidentally with the silver on the carrier. Suitable alkali metal salts are generally those which are soluble in the silver-impregnating liquid phase. Besides the above-mentioned compounds may be mentioned the nitrites; the halides, such as fluorides, chlorides, iodides, bromides; oxyhalides; bicarbonates; borates; sulfates; sulfites; bisulfates; acetates; tartrates; lactates and isopropoxides, etc. The use of alkali metal, rhenium or co-promoter salts which have ions which react with the silver salt in solution is preferably avoided, e.g. the use of cesium chloride together with silver nitrate in an aqueous solution, since then some silver chloride is prematurely precipitated. Here the use of cesium nitrate is recommended instead of cesium chloride, for example. However, cesium chloride may be used together with a silver salt-amine-complex in aqueous solution, since then the silver chloride is not precipitated prematurely from the solution.

The promoters may be deposited on the carrier (support) or on the catalyst, depending upon the particular impregnation technique or sequence utilized. In this specification and claims, the term "on the catalyst" when referring to the deposition or presence of promoters and/or co-promoters refers to the catalyst which comprises the combination of carrier (support) and silver. Thus, the promoters, i.e., alkali metal, rhenium and rhenium co-promoter may be found individually or in a mixture thereof on the catalyst, on the support or on both the catalyst and the support. There may be, for example, alkali, rhenium and rhenium co-promoter on the support, alkali, rhenium and rhenium co-promoter on the catalyst; alkali on the support and rhenium and rhenium co-promoter on the catalyst; alkali and rhenium on the support and rhenium co-promoter on the catalyst; alkali and rhenium co-promoter on the support and rhenium on the catalyst; alkali, rhenium and rhenium co-promoter on the support and rhenium and rhenium co-promoter on the catalyst and any of the other possible distributions of alkali, rhenium and/or rhenium co-promoter between the support and/or the catalyst.

The amount of the alkali metal and/or rhenium promoters and/or rhenium co-promoters on the porous carrier or catalyst may also be regulated within certain limits by washing out the surplus of promoter material with an appropriate solvent, for example, methanol or ethanol.

A particularly preferred process of impregnating the carrier consists of impregnating the carrier with an aqueous solution containing a silver salt of a carboxylic acid, an organic amine, a salt of cesium, ammonium perrhenate and ammonium sulfate dissolved therein. Silver oxalate is a preferred salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound, ammonium perrhenate and ammonium sulfate. While addition of the amine to the silver oxide before adding the oxalic acid is possible, it is not preferred since it can give rise to solutions which are unstable or even explosive in nature. Other diamines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water and ammonium perrhenate and ammonium sulfate is added. Rubidium-, potassium-, sodium-, lithium- and mixtures of alkali metal-containing solutions may be prepared also in these ways. The impregnated carriers are then heated to a temperature between 50° C. and 600° C., preferably between 75° C. and 400° C. to evaporate the liquid and produce a metallic silver.

In general terms, the impregnation process comprises impregnating the support with one or more solutions comprising silver, alkali metal, rhenium and rhenium co-promoter. As used in the instant specification and claims, the terminology "impregnating the support with one or more solutions comprising silver, alkali metal, rhenium and/or rhenium co-promoter" and similar or cognate terminology means that the support is impregnated in a single or multiple impregnation with one solution containing silver, alkali metal, rhenium and rhenium co-promoter; in multiple impregnations with two or more solutions containing silver, alkali metal, rhenium and rhenium co-promoter in differing amounts; or in multiple impregnations with two or more solutions, wherein each solution contains at least one component selected from silver, alkali metal, rhenium and rhenium co-promoter with the proviso that all of the components of silver, alkali metal, rhenium and rhenium co-promoter will individually be found in at least one of the solutions. The concentration of the silver (measured as the metal) in the silver-containing solution will range from about 1 g/l up to the solubility limit of silver in the solution and preferably from about 10 g/l up to the solubility limit when a single impregnation is utilized. The concentration of the alkali metal (measured as the metal) will range from about $1 \times 10^{-3}$ g/l up to about 12 g/l and preferably from about $10 \times 10^{-3}$ g/l to about 12 g/l when a single impregnation is utilized. The concentration of the rhenium (measured as the metal) will range from about $5 \times 10^{-3}$ g/l to about 20 g/l and preferably from about $50 \times 10^{-3}$ g/l to about 20 g/l when a single impregnation step is utilized. The concentration of rhenium co-promoter (measured as the element) will range from about $1 \times 10^{-3}$ g/l to about 20 g/l and preferably from about $10 \times 10^{-3}$ g/l to about 20 g/l when a single impregnation step is utilized. Concentrations selected within the above noted ranges will depend upon the pore volume of the catalyst, the final amount desired in the final catalyst and whether the impregnation is single or multiple. Appropriate concentrations can readily be determined by routine experimentation.

The amount of silver deposited on the support or present on the support is to be a catalytically effective amount of silver, i.e., an amount that catalyzes the reaction of ethylene and oxygen to produce ethylene oxide. Preferably this amount will range from about 1 to about 30 percent by weight of the total catalyst, more preferably from about 1 to about 25 percent by weight of the total catalyst and even more preferably from about 5 to about 20 percent by weight of the total catalyst. The upper and lower limits of preferred silver concentrations can be suitably varied, depending upon the particular catalytic properties or effect desired or the other variables involved. Possible lower limits of silver are, for example, about 1, 3, 5, 6, 8 and 10 per cent by weight of the total catalyst. Possible upper limits of silver are, for example, about 15, 16, 18, 20, 22, 25 and 30 percent by weight of the total catalyst.

The amount of alkali metal deposited on the support or catalyst or present on the support or catalyst is to be a promoting amount. Preferably the amount will range from about 10 to about 3000, more preferably from about 15 to about 2000 and even more preferably from about 20 to about 1500 and yet even more preferably from about 50 to about 1000 ppm by weight of the total catalyst, measured as the metal. The upper and lower limits of preferred alkali metal concentrations can be suitably varied depending upon the particular promoting effect desired or other variables involved. Possible lower limits of alkali metal are, for example, about 1, 5, 10, 25, 50, 75, 100, 200 and 300 ppm by weight of the total catalyst, measured as the metal. Possible upper limits of alkali metal are, for example, about 250, 300, 400, 500, 600, 700, 800, 900, 1000, 1250, 1500, 2000, 2500 and 3000 ppm by weight of the total catalyst, measured as the metal.

The amount of rhenium deposited on the support or catalyst or present on the support or catalyst is to be a promoting amount. Preferably the amount will range from about 0.01 to about 15, more preferably from about 0.1 to about 10, even more preferably from about 0.2 to about 5 and yet even more preferably from about 0.5 to about 4 $\mu$moles/g of total catalyst, measured as the metal. The upper and lower limits of preferred rhenium concentrations can be suitably varied depending upon the particular promoting effect desired or other variables involved. Possible lower limits of rhenium are, for example, about 0.01, 0.1, 0.2, 0.25, 0.3, 0.4, 0.5, 0.6, 0.7, 0.8, 0.9, 1 and 1.5 $\mu$moles/g of total catalyst. Possible upper limits of rhenium are, for example, about 2.5, 3, 4, 5, 6, 7, 8, 9, 10, 12, 14, 15 and 16 $\mu$moles/g of total catalyst.

The amount of rhenium co-promoter deposited on the support or catalyst or present on the support or catalyst is to be a promoting amount. Preferably the amount will range from about 0.01 to about 15, more preferably from about 0.1 to about 10, even more preferably from about 0.2 to about 5 and yet even more preferably from about 0.5 to about 4 $\mu$moles/g of total catalyst, measured as the metal. The upper and lower limits of preferred rhenium co-promoter concentrations can be suitably varied depending upon the particular promoting effect desired or other variables involved. Possible lower limits of rhenium co-promoter are, for example, about 0.01, 0.1, 0.2, 0.25, 0.3, 0.4, 0.5, 0.6, 0.7, 0.8, 0.9, 1 and 1.5 $\mu$moles/g of total catalyst. Possible upper limits of rhenium co-promoter are, for example, about 2.5, 3, 4, 5, 6, 7, 8, 9, 10, 12, 14, 15 and 16 $\mu$moles/g of total catalyst.

It is observed that independent of the form in which the silver is present in the solution before precipitation on the carrier, the term "reduction to metallic silver" is used, while in the meantime often decomposition by heating occurs. We prefer to use the term "reduction", since the positively charge Ag+ion is converted into metallic Ag atom. Reduction times may generally vary from about 0.5 minute to about 8 hours, depending on the circumstances.

The silver catalysts according to the present invention have been shown to have a particularly high initial selectivity for ethylene oxide in the direct oxidation of ethylene with molecular oxygen to ethylene oxide. The conditions for carrying out such an oxidation reaction in the presence of the silver catalysts according to the present invention broadly comprise those already described in the prior art. This applies, for example, to suitable temperatures, pressures, residence times, diluent materials, such as nitrogen, carbon dioxide, steam, argon, methane or other saturated hydrocarbons, presence of moderating agents to control the catalytic action, for example, 1-2-dichloroethane, vinyl chloride or chlorinated polyphenyl compounds, the desirability of employing recycle operations or applying successive conversions in different reactors to increase the yields of ethylene oxide, and any other special conditions which may be selected in processes for preparing ethylene oxide. Pressures in the range of from atmospheric to 35 bar are generally employed. Higher pressures are, however, by no means excluded. Molecular oxygen employed as reactant can be obtained from conventional sources. The suitable oxygen charge may consist essentially of relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxidation reactions is in no way limited to the use of specific conditions among those which are known to be effective. For purposes of illustration only, the following table shows the range of conditions that are often used in current commercial ethylene oxide reactor units.

TABLE 2

| *GHSV | 1500–10,000 |
|---|---|
| Inlet pressure | 150–400 psig |
| Inlet Feed | |
| ethylene | 1–40% |
| $O_2$ | 3–12% |
| $CO_2$ | 2–40% |
| ethane | 0–3% |
| Argon and/or methane and/or nitrogen | |
| diluent chlorohydrocarbon moderator | 0.3–20 ppmv total |
| Coolant temperature | 180–315° C. |
| Catalyst temperature | 180–325° C. |
| $O_2$ conversion level | 10–60% |
| EO Production (Work Rate) | 2–16 lbs. EO/cu. ft. catalyst/hr. |

*Liters of gas at standard temperature and pressure passing over one liter of packed catalyst per hour.

In a preferred application of the silver catalysts according to the present invention, ethylene oxide is produced when an oxygen-containing gas is contacted with ethylene in the presence of the present catalysts at a temperature in the range of from about 180° C. to about 330° C. and preferably about 200° C. to about 325° C.

The invention will be illustrated by the following illustrative embodiments which are provided for illustration only and are not intended to limit the scope of the instant invention.

ILLUSTRATIVE EMBODIMENTS

Illustrative Embodiment 1

The following illustrative embodiment describes typical preparative techniques for making the catalysts of the instant invention (and comparative catalysts) and the typical technique for measuring the properties of these catalysts.

Part A: Preparation of stock silver oxalate/ethylenediamine solution for use in catalyst preparation:

(1) Dissolve 415g reagent-grade NaOH in 2340 ml deionized water. Adjust temperature to 50° C.

(2) Dissolve 1699 g "spectropure" (high-purity) $AgNO_3$ in 2100 ml deionized water. Adjust temperature to 50° C.

(3) Add NaOH solution slowly to $AgNO_3$ solution with stirring, maintaining temperature at 50° C. Stir for 15 minutes after addition is complete, then lower temperature to 40° C.

(4) Insert clean filter wands and withdraw as much water as possible from the precipitate created in step (3) in order to remove sodium and nitrate ions. Measure the conductivity of the water removed and add back as much fresh deionized water as was removed by the filter wands. Stir for 15 minutes at 40° C. Repeat this process until the conductivity of the water removed is less than 90 $\mu$mho/cm. Then add back 1500 ml deionized water.

(5) Add 630g of high-purity oxalic acid dihydrate in approximately 100g increments. Keep the temperature at 40° C. and stir to mix thoroughly. Add the last portion of oxalic acid dihydrate slowly and monitor pH to ensure that pH does not drop below 7.8. Aim for a pH endpoint of 8.0-8.4. Add high-purity silver oxide if necessary to achieve this endpoint.

(6) Remove as much water from the mixture as possible using clean filter wands in order to form a highly concentrated silver-containing slurry. Cool the silver oxalate slurry to 30° C.

(7) Add 699g of 92%w ethylenediamine (8% deonized water). Do not allow the temperature to exceed 30° C. during addition.

The above procedure yields a solution containing approximately 27-33 %w Ag.

Part B: Catalyst Impregnation Procedures

Catalyst support Example B described in Table 1 is a preferred support for the instant invention and is used in the following examples and illustrative embodiments unless otherwise stated.

Preparation of undoped impregnating solution is as follows: The stock Ag oxalate/ethylenediamine solution of Part A is diluted preferably with deionized water, or alternatively may be diluted with monoethanolamine, or a mixture of deionized water and monoethanolamine to achieve a Ag concentration of approximately 27.6% by weight. The use of monoethanolamine or monoethanolamine plus water to dilute the stock solution is believed to provide catalysts comparable to those obtained by the use of water. However, it is believed that certain impurities present in monoethanolamine can cause inconsistent results in the catalysts made with monoethanolamine. Hence, water is preferred and was used for all of the examples provided herein.

Preparation of doped impregnation solution is as follows:

For catalyst A (Cs only): Add 46.4 mg of aqueous CsOH solution (50.7% w Cs) directly to 50g of undoped impregnating solution.

For catalyst B (Cs - Re): Dissolve 55.0 mg of $NH_4ReO_4$ in a minimum volume of 50/50 (w/w) ethylenediamine/deionized water and add to 50g of undoped impregnating solution. Then add 84.7 mg of aqueous CsOH solution (50.7%w Cs) to the same impregnating solution.

For catalyst C(Cs-Re-S): Dissolve 27.4 mg of $NH_4ReO_4$ plus 13.5 mg of $(NH_4)SO_4$ in a minimum volume of 50/50 (w/w) ethylenediamine/deionized water and add to 50g of undoped impregnating solution. Then add 82.7 mg of aqueous CsOH solution (50.7 %wt Cs) to the same impregnating solution.

The aqueous cesium hydroxide solution used for catalyst preparation in this and the following illustrative embodiments was doped with a radioactive isotope of cesium ($^{134}Cs$) so that the cesium levels on the finished catalysts could be readily determined by radiotracer analysis. (Alternatively, the levels of cesium and other alkali promoters on finished catalysts can be determined by the water leaching method described below.) The concentration of cesium in this aqueous, radiolabeled cesium hydroxide solution was determined to be 50.7 w% by neutron activation analysis at the Nuclear Science Center, Texas A&M University, College Station, Tex., using a TRIGA reactor, an Ortec high-purity Germanium Model BA-GEM-25185 detector, and a Tracor Northern Model 4000 multichannel analyzer. All target and actual cesium levels reported for catalysts in this and the following Illustrative Embodiments are based upon a value of 50.7 %w for the concentration of cesium in the stock, radiolabeled cesium hydroxide solution. However, when this same cesium hydroxide solution was subsequently analyzed by inductively coupled plasma jet-mass spectrometry using a SCIEZ Elan 250 instrument, the cesium concentration was found to be 45 %w. If this latter value for the cesium concentration in this solution is closer to the actual value, then the absolute levels of cesium for the catalysts described in this and the following Illustrative Embodiments would be approximately 11.2% lower than those reported.

Part C: Catalyst impregnation and curing

Approximately 30g of carrier B are placed under 25 mm vacuum for 3 minutes at room temperature. Approximately 50g of doped impregnating solution is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. If the impregnating solution is prepared without monoethanolamine, then the impregnated carrier is then cured by being continuously shaken in a 300 cu. ft./hr. air stream flowing across a cross-sectional area of approximately 3-5 square inches at 250° C. for 5 minutes. If significant monoethanolamine is present in the impregnating solution, then the impregnated carrier is cured by being continuously shaken in a 300 cu. ft./hr. air stream at 250° C. for 2.5 minutes, followed by a 100 cu. ft./hr. air stream at 270° C. for 7.5 minutes (all over a cross-section area of approximately 3-5 square inches). The cured catalyst is then ready for testing.

This procedure will yield catalysts on this carrier containing approximately 13.5% w Ag with the following approximate dopant levels and which are approximately optimum in cesium for the given silver and rhenium and sulfur levels and support with regard to initial selectivity under the test conditions described below.

|            | Cs, ppmw | Re, ppmw | S, ppm |
|------------|----------|----------|--------|
| catalyst A | 230      | 0        | 0      |
| B          | 420      | 372      | 0      |
| C          | 410      | 186      | 32     |

The actual silver content of the catalyst can be determined by any of a number of standard, published procedures. The actual level of rhenium on the catalysts prepared by the above process can be determined by extraction with 20 mM aqueous sodium hydroxide, followed by spectrophotometric determination of the rhenium in the extract, as described above. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D: Standard Microreactor Catalyst Test Conditions/Procedure 3 to 5g of crushed catalyst (14–20 mesh) are loaded into a ¼ inch diameter stainless steel U-shaped tube. The U tube is immersed in a molten metal bath (heat medium) and the ends are connected to a gas flow system. The weight of catalyst used and the inlet gas flow rate are adjusted to achieve a gas hourly space velocity of 3300 cc of gas per cc of catalyst per hour. The inlet gas pressure is 210 psig.

The gas mixture passed through the catalyst bed (in once-through operation) during the entire test run (including startup) consists of 30% ethylene, 8.5% oxygen, 7% carbon dioxide, 54.5% nitrogen, and 4.4 to 5.6 ppmv vinyl chloride.

The initial reactor (heat medium) temperature is 180° C. After 1 hour at this initial temperature, the temperature is increased to 190° C. for 1 hour, followed by 200° C. (1 hour), 210° C. (1 hour), 220° C. (1 hour), 227° C. (2 hours), 235° C. (2 hours), and 242° C. (2 hours). The temperature is then adjusted so as to achieve a constant oxygen conversion level of 40%. Performance data at this conversion level are usually obtained when the catalyst has been onstream for a total of 16±4 hours and are referred to as "initial performance data" in the examples given below. Due to slight differences in feed gas composition, gas flow rates, and the calibration of analytical instruments used to determine the feed and product gas compositions, the measured selectivity and activity of a given catalyst may vary slightly from one test run to the next. To allow meaningful comparison of the performances of catalysts tested at different times, all catalysts described in this and the following illustrative embodiments were tested simultaneously with a standard catalyst having the composition of catalyst A or with a different catalyst which has been standardized with reference to catalyst A. All performance data reported in this and the following illustrative embodiments are corrected and stated relative to the average initial performance of catalyst A ($S_{40}$ = 80.0%; $T_{40}$ = 242° C.).

Typical initial performances at 40% $O_2$ conversion for the above recipes are as follows:

| catalyst A | selectivity = 80.0% | temperature = 242° C. |
|---|---|---|
| B | 81.9% | 248° C. |
| C | 82.9% | 253° C. |

Illustrative Embodiment 2

Using the general preparative technique of Illustrative Embodiment 1, a series of catalysts were prepared utilizing carrier B described in Table 1. The catalysts were prepared without using monoethanolamine. One series of catalysts contained 2 mmol (millimoles) of rhenium per kilogram of catalyst, the second series contained 1 mmol of rhenium and 1 mmol of sulfur per kilogram of catalyst and the third series of catalysts was made in the identical fashion except that they contained no rhenium or no sulfur. In all three series the concentration of cesium in the individual catalysts was varied. The catalysts were tested as described in Illustrative Embodiment 1 and the results are shown in Table 3. The cesium levels reported in Table 3 were obtained by the radiotracer analysis technique described in Illustrative Embodiment 1, assuming a concentration of 50.7 %w cesium for the radiolabeled, aqueous cesium hydroxide solution used in catalyst preparation. Further, the results from these tests in the form of the initial selectivity versus cesium concentration are plotted in FIG. 1. In this Figure one can see the beneficial effects of rhenium plus sulfur which are indicated by the highlighted area between the two curves A and C to the right of their crossover point. It can be seen from the Figure that the use of rhenium plus sulfur provides not only an increase in the absolute value of the initial selectivity obtained at optimum cesium concentration, but also a significantly improved initial selectivity of the catalyst at high cesium concentrations, e.g., 300 ppm cesium and over when compared to catalysts containing no rhenium. The addition of the co-promoter also provides a higher initial selectivity over the case where no co-promoter is used.

Illustrative Embodiment 3

A series of catalysts were prepared in a fashion similar to the technique described in Illustrative Embodiment 1 using different carriers having those properties described in Table 1 in the specification. The catalysts were made without monoethanolamine. The catalysts were tested as described in Illustrative Embodiment 1 and the results are shown below in Table 4. Unless otherwise noted, all catalysts listed in Table 4 have cesium levels which give the optimum (highest) initial selectivity obtained under these conditions for a catalyst made on the indicated carrier with the indicated levels of silver and rhenium. The cesium levels reported in Table 4 were obtained by the radiotracer analysis technique described in Illustrative Embodiment 1, assuming a concentration of 50.7 %w cesium for the radiolabeled, aqueous cesium hydroxide solution used in catalyst preparation.

Illustrative Embodiment 4

A series of catalysts were prepared in a fashion similar to that described in Illustrative Embodiment 1 utilizing the support described in Illustrative Embodiment 2, but utilizing different rhenium and sulfur concentrations. The catalysts were tested as described in Illustrative Embodiment 1 and the results are shown in Table 5 below. Unless otherwise noted, all catalysts listed in Table 5 have cesium levels which give the optimum (highest) initial selectivity obtained under these test conditions for a catalyst made on this support with the indicated levels of silver, rhenium and sulfur. The cesium levels reported in Table 5 were obtained by the radiotracer analysis technique described in Illustrative Embodiment 1, assuming a concentration of 50.7 %w cesium for the radiolabeled, aqueous cesium hydroxide solution used in catalyst preparation.

Illustrative Embodiment 5

A series of catalysts were prepared in a fashion similar to that described in Illustrative Embodiment 1 using the support described in Illustrative Embodiment 2. The catalysts were made without monoethanolamine. In this series different alkali metals were utilized as alkali metal hydroxides. The catalysts were tested as described in Illustrative Embodiment 1 and the results are shown in Table 6 below. Unless otherwise noted, all catalysts listed in Table 6 have alkali levels which give the optimum (highest) initial selectivity obtained under these test conditions for a catalyst made with the indicated alkali metal hydroxide on this support with the indicated levels of silver, rhenium and sulfur. The alkali levels presented represent target levels.

Illustrative Embodiment 6

A series of catalysts were prepared in a fashion similar to that described in Illustrative Embodiment 1 using the support described in Illustrative Embodiment 2. In this series different combinations of alkali promoter(s), rhenium and rhenium co-promoter(s) were utilized. The catalysts were tested as described in Illustrative Embodiment 1 and the results are shown in Table 7 below.

Unless otherwise noted, all catalysts listed in Table 7 have cesium (or other alkali) levels which give the optimum (highest) initial selectivity obtained under these test conditions for a catalyst made on this support with the indicated levels of silver, rhenium, and rhenium co-promoter(s) and (if added) other alkali(s). The cesium levels reported in Table 7 were obtained by the radiotracer analysis technique described in Illustrative Embodiment 1, assuming a concentration of 50.7 %w cesium for the radiolabeled, aqueous cesium hydroxide solution used in catalyst preparation. The levels of the other alkalis given in Table 7 represent target levels. Catalyst 7-31 utilized a support which was comparable to Example B but which had a surface area of 0.45 $m^2/g$ instead of 0.42 $m^2/g$ and had about 10-15% lower levels of leachable sodium

TABLE 3
CS OPTIMIZATION ON CS ONLY; CS/RE; AND CS/RE + S CATALYSTS

| Experiment No. | % wAg | Re Target Level, ppmw | S Target Level, ppmw | Cs, ppmw (Radiotracer Analysis) | Initial $S_{40}$, % | Initial $T_{40}$, °C. |
|---|---|---|---|---|---|---|
| 3-1*** | 13.6 | 0 | 0 | 0 | 74.6 | 229 |
| 3-2*** | 13.6 | 0 | 0 | 104 | 77.6 | 232 |
| 3-3 | 14.3 | 0 | 0 | 236 | 80.0 | 242 |
| 3-4 | 14.3 | 0 | 0 | 301 | 79.4 | 243 |
| 3-5*** | 13.6 | 0 | 0 | 416 | 77.0 | 259 |
| 3-6 | 14.3 | 372* | 0 | 0 | 54.3 | 236 |
| 3-7 | 14.3 | 372 | 0 | 110 | 69.9 | 243 |
| 3-8 | 14.3 | 372 | 0 | 209 | 75.8 | 239 |
| 3-9 | 14.3 | 372 | 0 | 327 | 79.8 | 240 |
| 3-10 | 14.2 | 372 | 0 | 403 | 81.8 | 245 |
| 3-11 | 14.2 | 372 | 0 | 438 | 81.9 | 248 |
| 3-12 | 14.2 | 372 | 0 | 488 | 81.4 | 250 |
| 3-13 | 14.2 | 372 | 0 | 512 | 81.0 | 251 |
| 3-14 | 14.2 | 372 | 0 | 561 | 80.3 | 256 |
| 3-15*** | 13.8 | 186** | 32 | 0 | 61.2 | 232 |
| 3-16*** | 13.8 | 186 | 32 | 101 | 70.5 | 235 |
| 3-17*** | 13.8 | 186 | 32 | 208 | 77.2 | 241 |
| 3-18*** | 13.8 | 186 | 32 | 303 | 80.8 | 247 |
| 3-19 | 12.7 | 186 | 32 | 372 | 82.4 | 250 |
| 3-20*** | 13.8 | 186 | 32 | 402 | 83.0 | 253 |
| 3-21 | 12.7 | 186 | 32 | 421 | 82.9 | 253 |
| 3-22 | 12.7 | 186 | 32 | 450 | 82.7 | 255 |
| 3-23*** | 13.8 | 186 | 32 | 515 | 81.7 | 261 |

*2.0 μmoles/g
**1.0 μmoles/g
***Performance data at 40% oxygen conversion obtained when catalyst had been onstream for 32 ± 4 hours.

TABLE 4
CS-OPTIMIZED CATALYSTS ON DIFFERENT CARRIERS WITH AND WITHOUT RE/S

| Experiment No. | % wAg | Carrier | Cs, ppmw (Radiotracer Analysis) | Re Target Level ppmw | S Target Level ppmw | Initial $S_{40}$, % | Initial $T_{40}$, °C. |
|---|---|---|---|---|---|---|---|
| 4-1 | 10.3 | A | 162 | 0 | 0 | 80.1 | 248 |
| 4-2 | 10.6 | A | 234 | 93* | 16* | 82.9 | 262 |
| 4-3 | 14.3 | B | 236 | 0 | 0 | 80.3 | 240 |
| 4-4 | 12.7 | B | 421 | 186** | 32** | 82.9 | 253 |
| 4-5 | 14.1 | C | 256 | 0 | 0 | 80.3 | 240 |
| 4-6 | 14.4 | C | 395 | 186 | 32 | 83.4 | 255 |
| 4-7 | 15.0 | D | 309 | 0 | 0 | 80.9 | 240 |
| 4-8 | 14.9 | D | 482 | 186 | 32 | 84.1 | 260 |
| 4-9 | 14.6 | E | 386 | 0 | 0 | 80.0 | 241 |
| 4-10 | 14.1 | E | 540 | 186 | 32 | 83.3 | 264 |
| 4-11 | 19.0 | F | 637 | 0 | 0 | 80.4 | 235 |
| 4-12 | 18.2 | F | 899*** | 186 | 32 | 81.2 | 241 |

*0.5 μmoles/g
**1.0 μmoles/g
***may not be fully optimized with respect to Cs

TABLE 5
EFFECT OF DIFFERENT RELATIVE AND ABSOLUTE AMOUNTS OF RE AND S ON CESIUM OPTIMIZED CATALYST PERFORMANCE

| Experiment No. | % wAg | Cs, ppmw (Radiotracer Analysis) | Re Target Level, ppmw, (μmole/g) | S Target Level, ppmw, (μmole/g) | Initial $S_{40}$, % | Initial $T_{40}$, °C. |
|---|---|---|---|---|---|---|
| 5-1 | 14.3 | 236 | 0 | 0 | 80.0 | 242 |
| 5-2 | 13.8 | 297 | 93(0.5) | 0 | 80.4 | 246 |
| 5-3 | 13.9 | 360 | 186(1.0) | 0 | 80.6 | 241 |
| 5-4 | 14.2 | 438 | 372(2.0) | 0 | 81.9 | 248 |
| 5-5 | 14.5 | 486 | 465(2.5) | 0 | 82.3 | 248 |
| 5-6 | 14.1 | 567 | 558(3.0) | 0 | 82.5 | 248 |
| 5-7 | 14.0 | 634 | 744(4.0) | 0 | 80.2 | 248 |
| 5-8 | 14.2 | 341 | 0 | 32(1.0) | 80.8 | 243 |
| 5-9 | 12.7 | 421 | 186(1.0) | 32(1.0) | 82.9 | 254 |
| 5-10 | 14.1 | 552 | 372(2.0) | 32(1.0) | 84.3 | 254 |
| 5-11 | 13.8 | 505 | 186(1.0) | 64(2.0) | 82.0 | 273 |
| 5-12 | 12.8 | 513 | 372(2.0) | 64(2.0) | 81.7 | 274 |

TABLE 6

OPTIMIZATION WITH DIFFERENT ALKALIS, WITH AND WITHOUT RE AND RE + S

| Experiment No. | % wAg | Alkali Dopant Added | Target ppmw Alkali | Re Target Level, ppmw | Target S Level ppmw | Initial $S_{40}$, % | Initial $T_{40}$, °C. |
|---|---|---|---|---|---|---|---|
| 6-1 | 13.6 | None | 0 | 0 | 0 | 74.6 | 229 |
| 6-2 | 14.3 | None | 0 | 372* | 0 | 54.3 | 236 |
| 6-3 | 13.8 | None | 0 | 186** | 32*** | 61.2 | 232 |
| 6-4 | 14.3 | Cs | 230 | 0 | 0 | 80.0 | 242 |
| 6-5 | 14.2 | Cs | 420 | 372 | 0 | 81.9 | 248 |
| 6-6 | 12.7 | Cs | 410 | 186 | 32 | 82.9 | 253 |
| 6-7 | 14.0 | Rb | 170 | 0 | 0 | 79.4 | 238 |
| 6-8 | 14.6 | Rb | 305 | 372 | 0 | 80.0 | 246 |
| 6-9 | 14.3 | Rb | 325 | 186 | 32 | 81.2 | 248 |
| 6-10 | 14.6 | K | 130 | 0 | 0 | 79.4 | 240 |
| 6-11 | 14.5 | K | 200 | 372 | 0 | 78.1 | 239 |
| 6-12 | 14.1 | K | 250 | 186 | 32 | 78.6 | 241 |
| 6-13 | 14.4 | Na | 207 | 0 | 0 | 76.5 | 234 |
| 6-14 | 14.7 | Na | 92 | 372 | 0 | 74.3 | 246 |
| 6-15 | 14.5 | Na | 253 | 186 | 32 | 75.9 | 241 |
| 6-16 | 13.9 | Li | 40 | 0 | 0 | 74.8 | 233 |
| 6-17 | 14.2 | Li | 120 | 372 | 0 | 63.5 | 239 |
| 6-18 | 13.7 | Li | 100 | 186 | 32 | 68.2 | 234 |

*2.0 μmoles/g
**1.0 μmoles/g
***1.0 μmoles/g

TABLE 7

EFFECT OF VARIOUS RHENIUM CO-PROMOTERS ON CATALYST PERFORMANCE

| Experiment No. | % wAg | Alkali metal[a] ppmw | Re Target[b] Level, ppmw (μmole/g) | Re Co-promoter (Salt Added) | Co-Promoter Element, Target Level, ppmw (μmole/g) | Initial $S_{40}$, % | Initial $T_{40}$, °C. |
|---|---|---|---|---|---|---|---|
| 7-1 | 14.3 | 236 Cs | 0 | None | 0 | 80.0 | 242 |
| 7-2 | 13.9 | 360 Cs | 186(1.0) | None | 0 | 80.6 | 241 |
| 7-3 | 14.2 | 438 Cs | 372(2.0) | None | 0 | 81.9 | 248 |
| 7-4 | 13.3 | 405 Cs[h] | 186(1.0) | $(NH_4)_2SO_4$ | S,32(1.0) | 83.1 | 259 |
| 7-5 | 13.7 | 392 Cs | 186(1.0) | $(NH_4)_2SO_3$ | S,32(1.0) | 82.9 | 250 |
| 7-6 | 12.7 | 421 Cs | 186(1.0) | $(NH_4)_2SO_4$ | S,32(1.0) | 82.9 | 253 |
| 7-7 | 13.8 | 505 Cs | 186(1.0) | $(NH_4)_2SO_4$ | S,64(2.0) | 82.0 | 273 |
| 7-8 | 13.7 | 419 Cs | 186(1.0) | p-toluene-sulfonic acid | S,32(1.0) | 83.6 | 256 |
| 7-9[i] | 13.1 | 394 Cs | 186(1.0) | $(NH_4)_2CrO_4$ | Cr,52(1.0) | 82.9 | 269 |
| 7-10 | 13.9 | 393 Cs | 186(1.0) | $(NH_4)_2Mo_2O_7$ | Mo,96(1.0) | 83.5 | 267 |
| 7-11[i] | 14.1 | 389 Cs | 186(1.0) | $H_2WO_4$ | W,184(1.0) | 83.0 | 259 |
| 7-12 | 13.5 | 338 Cs | 186(1.0) | $KMnO_4$ | Mn,55(1.0) | 80.8 | 242 |
| 7-13 | 13.5 | 391 Cs | 186(1.0) | $NH_4ClO_4$ | Cl,35.5(1.0) | 80.6 | 244 |
| 7-14 | 14.3 | 463 Cs | 186(1.0) | $NH_4VO_3$ | V,51(1.0) | 79.5 | 277 |
| 7-15 | 13.8 | 375 Cs | 186(1.0) | $NH_4H_2PO_4$ | P,31(1.0) | 80.4 | 252 |
| 7-16 | 14.5 | 160 K | 186(1.0) | $(NH_4)_6Mo_7O_{24}.4H_2O$ | Mo,96(1.0) | 81.1 | 279 |
| 7-17 | 14.1 | 200 K | 186(1.0) | $H_2WO_4$ | W,184(1.0) | 79.3 | 260 |
| 7-18 | 14.4 | 160 K | 186(1.0) | $(NH_4)_2CrO_4$ | Cr,52(1.0) | 78.9 | 273 |
| 7-19 | 14.6 | 138 Na | 186(1.0) | $(NH_4)_6Mo_7O_{24}.4H_2O$ | Mo,96(1.0) | 75.3 | 257 |
| 7-20 | 14.3 | 255 Rb | 186(1.0) | $(NH_4)_6Mo_7O_{24}.4H_2O$ | Mo,96(1.0) | 82.8[c] | 269[c] |
| 7-21[i] | 14.1 | 138 Cs + 120 K | 186(1.0) | $(NH_4)_6Mo_7O_{24}.4H_2O$ | Mo,96(1.0) | 82.6 | 270 |
| 7-22 | 12.9 | 384 Cs + 46 Na[d] | 186(1.0) | $(NH_4)_2SO_4$ | S,64(2.0) | 83.3 | 260 |
| 7-23 | 13.3 | 383 Cs + 46 Na[d] | 186(1.0) | $(NH_4)_2CrO_4$ | Cr,52(1.0) S,32(1.0) | 83.0 | 269 |
| 7-24 | 13.6 | 404 Cs + 46 Na[d] | 186(1.0) | $H_2WO_4$ | W,184(1.0) S,32(1.0) | 83.8 | 260 |
| 7-25 | 13.4 | 394 Cs + 78 K[d] | 186(1.0) | $(NH_4)_2SO_4$ | S,64(2.0) | 83.1 | 258 |
| 7-26 | 14.7 | 387 Cs + 78 K[d] | 186(1.0) | $HWO_4$ | W,184(1.0) S,32(1.0) | 83.8 | 266 |
| 7-27 | 14.3 | 293 Cs + 7 Li[d] | 186(1.0) | $(NH_4)_2SO_4$ | S,32(1.0) | 82.4 | 245 |
| 7-28 | 13.7 | 407 Cs + 7 Li[d] + 46 Na[d] | 186(1.0) | $(NH_4)_2SO_4$ | S,64(2.0) | 84.9 | 259 |
| 7-29 | 13.9 | 380 Cs + 28 Li[e] | 186(1.0) | $(NH_4)_2CrO_4$ | Cr,52(1.0) | 83.6 | 272 |
| 7-30 | 13.6 | 380 Cs + 7 Li[e] | 186(1.0) | $(NH_4)_2SO_4$ | S,32(1.0) | 83.6 | 253 |
| 7-31 | 13.3 | 354 Cs + 39 K[f] | 372(2.0)[j] | $(NH_4)_2SO_4$ | S,32(1.0) | 83.1 | 260 |

TABLE 7-continued
EFFECT OF VARIOUS RHENIUM CO-PROMOTERS ON CATALYST PERFORMANCE

| Experiment No. | % wAg | Alkali metal[a] ppmw | Re Target[b] Level, ppmw (μmole/g) | Re Co-promoter (Salt Added) | Co-Promoter Element, Target Level, ppmw (μmole/g) | Initial $S_{40}$, % | Initial $T_{40}$, °C. |
|---|---|---|---|---|---|---|---|
| 7-32 | 13.7 | 393 Cs + 14 Li[g] | 186(1.0) | $(NH_4)_2SO_4$ | S,32(1.0) | 83.8 | 257 |

[a]radiotracer on Cs, target level on other alkali metals, alkali added as hydroxide unless otherwise noted.
[b]rhenium added to impregnating solution as $NH_4ReO_4$ unless otherwise noted.
[c]38% conversion data.
[d]as sulfate
[e]as nitrate
[f]1 μmole/g each of $NH_4ReO_4$ and $KReO_4$.
[g]as $LiBO_2$
[h]$CsNO_3$ used rather than CsOH in impregnating solution; target level indicated.
[i]may not be fully optimized with respect to cesium.
[j]may not be fully optimized with respect to potassium.

I claim:

1. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of alkali metal, a promoting amount of rhenium and a promoting amount of a rhenium co-promoter selected from sulfur, molybdenum, tungsten, chromium and mixtures thereof supported on a suitable support.

2. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising silver, alkali metal promoter, from about 0.2 to about 5 millimoles of rhenium promoter, measured as the metal, per kilogram of total catalyst, and from about 0.2 to about 5 millimoles, measured as the element, per kilogram of total catalyst, of a rhenium co-promoter comprising sulfur, molybdenum, tungsten, chromium or mixtures thereof supported on a porous, refractory support; the combination of silver, alkali metal promoter, rhenium promoter, rhenium co-promoter and support affording a higher selectivity to ethylene oxide at a given oxygen conversion level than is obtained under the same reaction conditions with the same combination of silver and support and none, one or two of the promoters selected from alkali metal, rhenium and rhenium co-promoter.

3. In a process for the production of ethylene oxide wherein ethylene is contacted in the vapor phase with an oxygen-containing gas at ethylene oxide forming conditions at a temperature ranging between about 180° C. to 330° C. in the presence of a fixed bed of silver metal-containing catalyst, the improvement which comprises using a catalyst comprising silver, alkali metal promoter, from about 0.2 to about 5 millimoles of rhenium, measured as the metal, per kilogram of total catalyst and from about 0.2 to about 5 millimoles, measured as the element, per kilogram of total catalyst, of a rhenium co-promoter selected from sulfur, molybdenum, tungsten, chromium and mixtures thereof, supported on a porous, refractory support wherein the rhenium is applied to the support in the form of a perrhenate or rhenium heptoxide and the rhenium co-promoter is applied to the support in the form of an oxidic compound or an oxyanion; the combination of silver, alkali metal promoter, rhenium, rhenium co-promoter and support affording a higher selectivity to ethylene oxide at a given oxygen conversion level than is obtained under the same reaction conditions with the same combination of silver and support and none, one or two of the promoters selected from alkali metal, rhenium and rhenium co-promoter.

4. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, alkali metal promoter, from about 0.2 to about 5 millimoles of rhenium, measured as the metal, per kilogram of total catalyst in a form which is extractable in a dilute (20 millimolar) aqueous solution of sodium hydroxide, and from about 0.2 to about 5 millimoles, measured as the element, per kilogram of total catalyst, of a rhenium co-promoter selected from sulfur, molybdenum, tungsten, chromium and mixtures thereof supported on a porous, refractory support; the combination of silver, alkali metal promoter, rhenium and rhenium co-promoter and support affording a higher selectivity to ethylene oxide at a given oxygen conversion level than is obtained under the same reaction conditions with the same combination of silver and support and none, one or two of the promoters selected from alkali metal, rhenium and rhenium co-promoter.

5. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, alkali alkali metal promoter, from about 0.2 to about 5 millimoles of rhenium, measured as the metal, per kilogram of total catalyst in a form which is extractable in a dilute (20 millimolar) aqueous solution of sodium hydroxide and from about 0.2 to about 5 millimoles, measured as the element, per kilogram of total catalyst, of rhenium co-promoter selected from sulfur, molybdenum, tungsten, chromium and mixtures thereof supported on a porous, refractory support wherein the rhenium is applied to the support in the form of a perrhenate or rhenium heptoxide and the rhenium co-promoter is applied to the support in the form of an oxidic compound or an oxyanion; the combination of silver, alkali metal promoter, rhenium, rhenium co-promoter and support affording a higher selectivity to ethylene oxide at a given oxygen conversion level than is obtained under the same reaction conditions with the same combination of silver and support and none, one or two of the promoters selected from alkali metal, rhenium and rhenium co-promoter.

6. The process of claims 1, 2, 3, 4 or 5 wherein in the catalyst the rhenium co-promoter comprises an oxidic compound.

7. The process of claim 6 wherein in the catalyst the support comprises alpha alumina.

8. The process of claim 7 wherein in the catalyst the support surface area ranges from about 0.05 to about 5 m$^2$/g.

9. The process of claim 8 wherein in the catalyst the support surface area ranges from about 0.1 to about 3 m$^2$/g.

10. The process of claim 9 wherein in the catalyst the silver ranges from about 1 to about 25 percent by weight of the total catalyst, and the alkali metal promoter ranges from about 20 to about 1500 parts by weight, measured as the metal, per million parts by weight of the total catalyst.

11. The process of claims 7, 8 or 9 wherein in the catalyst the alkali metal is cesium plus an alkali metal selected from the group consisting of lithium, sodium, potassium and mixtures thereof.

12. The process of claim 10 wherein in the catalyst the alkali metal is cesium plus lithium.

13. The process of claim 10 wherein in the catalyst the silver ranges from about 5 to about 20 percent by weight of the total catalyst and the alkali metal promoter ranges from about 50 to about 1000 parts by weight, measured as the metal, per million parts by weight of the total catalyst.

14. The process of claim 13 wherein in the catalyst the alkali metal, rhenium and rhenium co-promoter are found on the surface of the support or on the surface of the catalyst.

15. The process of claim 13 wherein in the catalyst the alkali metal, rhenium and rhenium co-promoter are found individually or in any mixture thereof on the catalyst, on the support or on both the catalyst and the support.

16. The process of claim 13 wherein in the catalyst said promoting amount of alkali metal, rhenium and rhenium co-promoter in combination with the silver and support is such as to provide a higher selectivity to ethylene oxide at a given oxygen conversion level than is obtained under the same reaction conditions with the same combination of silver and support and none, one or two of the promoters selected from alkali metal, rhenium and rhenium co-promoter.

17. The process of claim 16 wherein the selectivity is measured at an oxygen conversion level of about 40% at a gas hourly space velocity of about 3300 and when the catalyst has been placed on stream for about 16±4 hours.

18. The process of claims 16 or 17 wherein in the catalyt the alkali metal is cesium plus an alkali metal selected from the group consisting of lithium, sodium, potassium and mixtures thereof.

19. The process of claims 3 or 5 wherein in the catalyst the rhenium co-promoter which is applied to the support is selected from sulfate, sulfite, sulfonate, molybdate, tungstate, chromate and mixtures thereof.

20. The process of claim 19 wherein in the catalyst the support comprises alpha alumina, the silver ranges from about 1 to about 25 percent by weight of the total catalyst and the alkali metal promoter ranges from about 20 to about 1500 ppm by weight of the total catalyst.

21. The process of claim 20 wherein in the catalyst the silver ranges from about 5 to about 20 percent by weight and the alkali metal promoter ranges from about 50 to about 1000 ppm by weight.

22. The process of claims 19, 20 and 21 wherein in the catalyst the alkali is cesium plus an alkali metal selected from the group consisting of lithium, sodium, potassium and mixtures thereof.

23. The process of claim 21 wherein in the catalyst the selectivity is measured at an oxygen conversion level of about 40% at a gas hourly space velocity of about 3300 and when the catalyst has been placed on stream for about 16±4 hours.

24. The process of claim 23 wherein in the catalyst the alkali metal is cesium plus lithium.

25. The process of claim 1 wherein in the catalyst said promoting amount of alkali metal, rhenium and rhenium co-promoter in combination with the silver and support is such as to provide a higher selectivity to ethylene oxide at a given oxygen conversion level than is obtained under the same reaction conditions with the same combination of silver and support and none, one or two of the promoters selected from alkali metal, rhenium and rhenium co-promoter.

26. The process of claim 25 wherein in the catalyst the alkali metal is cesium plus an alkali metal selected from lithium, sodium, potassium and mixtures thereof.

27. The process of claim 25 wherein the selectivity is measured at an oxygen conversion level of about 40% at a gas hourly space velocity of about 3300 and when the catalyst has been placed onstream for about 16±4 hours.

28. The process of claim 27 wherein in the catalyst the alkali metal is cesium plus lithium.

29. The process of claim 1 wherein in the catalyst silver ranges from about 1 to about 25 percent by weight of the total catalyst, the alkali metal promoter ranges from about 20 to about 1500 parts by weight, measured as the metal, per million parts by weight of total catalyst, the rhenium ranges from about 0.2 to about 5 millimoles, measured as the element, per kilogram of total catalyst.

30. The process of claim 29 wherein in the catalyst the alkali metal is cesium plus an alkali metal selected from the group consisting of lithium, sodium, potassium and mixtures thereof.

31. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of a higher alkali metal comprising potassium, rubidium, cesium, or mixtures thereof, a promoting amount of rhenium and a promoting amount of a rhenium co-promoter comprising sulfur, molybdenum, tungsten, chromium or mixtures thereof, supported on a suitable support.

32. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of a higher alkali metal selected from the group consisting of potassium, rubidium, cesium and mixtures thereof, a promoting amount of rhenium and a promoting amount of a rhenium co-promoter selected from the group consisting of sulfur, molybdenum, tungsten, chromium and mixtures thereof, supported on a porous, refractory support.

33. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a comprising silver, a higher alkali metal promoter comprising potassium, rubidium, cesium or mixtures thereof, from about 0.2 to about 5 millimoles of rhenium, measured as the metal, per kilogram of total catalyst and from about 0.2 to about 5 millimoles, measured as the element per kilogram of total catalyst, of a rhenium co-promoter comprising sulfur, molybdenum, tungsten, chromium or mixtures thereof supported on a porous, refractory support; the combination of silver, higher alkali metal promoter, rhenium promoter, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

34. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof, from about 0.2 to about 5 millimoles of rhenium, measured as the metal, per kilogram of total catalyst and from about 0.2 to about 5 millimoles, measured as the element, per kilogram of total catalyst, of a rhenium co-promoter selected from sulfur, molybdenum, tungsten, chromium and mixtures thereof supported on a porous, refractory support wherein the rhenium is applied to the support in the form of a perrhenate or rhenium heptoxide and the rhenium co-promoter is applied to the support in the form of an oxidic compound or an oxyanion; the combination of silver, higher alkali metal promoter, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

35. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof, from about 0.2 to about 5 millimoles of rhenium, measured as the metal, per kilogram of total catalyst in a form which is extractable in a dilute (20 millimolar) aqueous solution of sodium hydroxide, and from about 0.2 to about 5 millimoles, measured as the element, per kilogram of total catalyst, or a rhenium co-promoter selected from sulfur, molybdenum, tungsten, chromium and mixtures thereof supported on a porous, refractory support; the combination of silver, higher alkali metal promoter, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

36. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof, from about 0.2 to about 5 millimoles of rhenium, measured as the metal, per kilogram of total catalyst in a form which is extractable in a dilute (20 millimolar) aqueous solution of sodium hydroxide and from about 0.2 to about 5 millimoles, measured as the element, per kilogram of total catalyst, of a rhenium co-promoter selected from sulfur, molybdenum, tungsten, chromium and mixtures thereof, supported on a porous, refractory support wherein the rhenium is applied to the support in the form of a perrhenate or rhenium heptoxide and the rhenium co-promoter is applied to the support in the form of an oxidic compound or an oxyanion; the combination of silver, higher alkali metal promoter, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

37. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof, from about 0.2 to about 5 millimoles of rhenium, measured as the metal, per kilogram of total catalyst and from about 0.2 to about 5 millimoles, measured as the element, per kilogram of total catalyst, of a rhenium co-promoter selected from sulfur, molybdenum, tungsten, chromium and mixtures thereof supported on a porous, refractory support comprising alpha alumina having a surface area ranging from about 0.1 to about 3 $m^2/g$ and a water pore volume ranging from about 0.25 to about 0.55 cc/gm; the combination of silver, higher alkali metal, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

38. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof, from about 0.2 to about 5 millimoles of rhenium, measured as the metal, per kilogram of total catalyst and from about 0.2 to about 5 millimoles, measured as the element, per kilogram of total catalyst, of a rhenium co-promoter selected from sulfur, molybdenum, tungsten, chromium and mixtures thereof supported on a porous, refractory support comprising alpha alumina having a surface area ranging from about 0.1 to about 3 $m^2/g$ and a water pore volume ranging from about 0.25 to about 0.55 cc/gm wherein the rhenium is applied to the support in the form of a perrhenate or rhenium heptoxide and the rhenium co-promoter is applied to the support in the form of an oxidic compound or an oxyanion; the combination of silver, higher alkali metal, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

39. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof, from about 0.2 to about 5 millimoles of rhenium, measured as the metal, per kilogram of total catalyst in a form which is extractable in a dilute (20 millimolar) aqueous solution of sodium hydroxide and from about 0.2 to about 5 millimoles, measured as the element, per kilogram of total catalyst, of a rhenium co-promoter selected from sulfur, molybdenum, tungsten, chromium and mixtures thereof supported on a porous, refractory support comprising alpha alumina having a surface area ranging from about 0.1 to about 3 $m^2/g$ and a water pore volume ranging from about 0.25 to about 0.55 cc/gm; the combination of silver, higher alkali metal, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium, rhenium co-promoter.

40. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof, from about 0.2 to about 5 millimoles of rhenium, measured as the metal, per kilogram of total catalyst in a form which is extractable in a dilute (20 millimolar) aqueous solution of sodium hydroxide and from about 0.2 to about 5 millimoles, measured as the element, per kilogram of total catalyst, of a rhenium co-promoter selected from sulfur, molybdenum, tungsten, chromium and mixtures thereof supported on a porous, refractory support comprising alpha alumina having a surface area ranging from about 0.1 to about 3 $m^2/g$ and a water pore volume ranging from about 0.25 to about 0.55 cc/gm wherein the rhenium is applied to the support in the form of a perrhenate or rhenium heptoxide and the rhenium co-promoter is applied to the support in the form of an oxidic compound or an oxyanion; the combination of silver, higher alkali metal, rhenium, rhenium co-promoter and support affording a higher selectivity to ethylene oxide at a given oxygen conversion level than is obtained under the same reaction conditions with the same combination of silver and support and none, one or two of the promoters selected from higher alkali metal, rhenium and rhenium co-promoter.

41. The process of any of claims 31-40 wherein in the catalyst the rhenium co-promoter comprises an oxidic compound.

42. The process of claim 41 wherein in the catalyst the support comprises alpha alumina.

43. The process of claim 42 wherein in the catalyst the support comprises alpha alumina which has a surface area ranging from about 0.05 to about 5 $m^2/g$ and a water pore volume ranging from about 0.10 to about 0.75 cc/g.

44. The process of claim 43 wherein in the catalyst the support surface area ranges from about 0.1 to about 3 $m^2/g$.

45. The process of claims 31 and 32 wherein in the catalyst the silver ranges from about 1 to about 25 percent by weight of the total catalyst, the higher alkali metal promoter ranges from about 20 to about 1500 parts by weight, measured as the metal, per million parts by weight of total catalyst, the rhenium ranges from about 0.2 to about 5 millimoles of rhenium, measured as the metal, per kilogram of total catalyst, the rhenium co-promoter ranges from about 0.2 to about 5 millimoles, measured as the element, per kilogram of total catalyst and the support comprises alpha alumina with a surface area ranging from about 0.05 to about 5 $m^2/g$.

46. The process of claim 45 wherein in the catalyst said promoting amount of higher alkali metal, rhenium and rhenium co-promoter in combination with the silver and support is such as to provide a higher selectivity to ethylene oxide at a given oxygen conversion level than is obtained under the same reaction conditions with the same combination of silver and support and none, one or two of the promoters selected from higher alkali metal, rhenium and rhenium co-promoter.

47. The process of claim 46 wherein the selectivity is measured at an oxygen conversion level of about 40% at a gas hourly space velocity of about 3300 and when 48. The process of claim 45 wherein in the catalyst the higher alkali metal ranges from about 50 to about 1000 ppm by weight.

49. The process of claim 48 wherein in the catalyst the higher alkali metal comprises potassium.

50. The process of claim 48 wherein in the catalyst the higher alkali metal comprises rubidium.

51. The process of claim 48 wherein in the catalyst the higher alkali metal comprises cesium.

52. The process of claim 48 wherein in the catalyst the higher alkali metal comprises potassium and cesium.

53. The process of claim 48 wherein in the catalyst the higher alkali metal comprises rubidium and cesium.

54. The process of claim 48 wherein in the catalyst the higher alkali metal comprises cesium, rubidium and potassium.

55. The process of claim 48 wherein in the catalyst the alkali metal, rhenium and rhenium co-promoter are found on the surface of the support.

56. The process of claim 48 wherein in the catalyst the alkali metal, rhenium and rhenium co-promoter are found on the surface of the catalyst.

57. The process of claim 48 wherein in the catalyst the alkali metal, rhenium and rhenium co-promoter are found individually or in any mixture thereof on the catalyst, on the support or on both the catalyst and the support.

58. The process of claims 33, 34, 35 or 36 wherein in the catalyst the silver ranges from about 1 to about 25 percent by weight of the total catalyst and the alkali metal promoter ranges from about 20 to about 1500 parts by weight, measured as the metal, per million parts by weight of the total catalyst.

59. The process of claim 58 wherein in the catalyst the silver ranges from about 5 to about 20 percent by weight of the total catalyst and the alkali metal promoter ranges from about 50 to about 1000 parts by weight, measured as the metal, per million parts by weight of the total catalyst.

60. The process of claim 59 wherein in the catalyst the alkali metal comprises potassium.

61. The process of claim 59 wherein in the catalyst the alkali metal comprises rubidium.

62. The process of claim 59 wherein in the catalyst the alkali metal comprises cesium.

63. The process of claim 59 wherein in the catalyst the alkali metal, rhenium and rhenium co-promoter are found on the surface of the catalyst.

64. The process of claim 59 wherein in the catalyst the alkali metal, rhenium and rhenium co-promoter are found on the surface of the support.

65. The process of claim 59 wherein in the catalyst the alkali metal, rhenium and rhenium co-promoter are found individually or in any mixture thereof on the catalyst, on the support or on both the catalyst and the support.

66. The process of claim 59 wherein in the catalyst said promoting amount of higher alkali metal, rhenium and rhenium co-promoter in combination with the silver and support is such as to provide a higher selectivity to ethylene oxide at a given oxygen conversion level than is obtained under the same reaction conditions with the same combination of silver and support and none, one or two of the promoters selected from higher alkali metal, rhenium and rhenium co-promoter.

67. The process of claim 66 wherein the selectivity is measured at an oxygen conversion level of about 40% at a gas hourly space velocity of about 3300 and when the catalyst has been placed onstream for about 16±4 hours.

68. The process of claims 37, 38, 39 or 40 wherein the silver ranges from about 5 to about 20 percent by weight.

69. The process of claims 37, 38, 39 or 40 wherein the alkali metal, rhenium and rhenium co-promoter are found on the surface of the support or on the surface of the catalyst.

70. The process of claims 37, 38, 39 or 40 wherein the alkali metal, rhenium and rhenium co-promoter are found individually or in any mixture thereof on the catalyst, on the support or on both the catalyst and the support.

71. The process of claims 34, 36, 38 or 40 wherein in the catalyst the rhenium co-promoter which is applied to the support is selected from sulfate, sulfite, sulfonate, molybdate, tungstate, chromate and mixtures thereof.

72. The process of claim 68 wherein in the catalyst the higher alkali metal comprises potassium.

73. The process of claim 68 wherein in the catalyst the higher alkali metal comprises rubidium.

74. The process of claim 68 wherein in the catalyst the higher alkali metal comprises cesium.

75. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of cesium, a promoting amount of rhenium and a promoting amount of rhenium co-promoter selected from sulfur, molybdenum, tungsten, chromium and mixtures thereof on a porous refractory support comprising alpha alumina.

76. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter, from about 0.2 to about 5 millimoles of rhenium promoter, measured as the metal, per kilogram of total catalyst and from about 0.2 to about 5 millimoles, measured as the element, per kilogram of total catalyst, of a rhenium co-promoter selected from sulfur, molybdenum, tungsten, chromium and mixtures thereof supported on a porous, refractory support comprising alpha alumina having a surface area ranging from about 0.1 to about 3 $m^2/g$ and a water pore volume ranging from about 0.25 to about 0.55 cc/gm; the combination of silver, cesium promoter, rhenium promoter, rhenium co-promoter and support affording a higher selectivity to ethylene oxide at a given oxygen conversion level than is obtained under the same reaction conditions with the same combination of silver and support and none, one or two of the promoters selected from cesium, rhenium and rhenium co-promoter.

77. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter, from about 0.2 to about 5 millimoles of rhenium, measured as the metal, per kilogram of total catalyst and from about 0.2 to about 5 millimoles, measured as the element, per kilogram of total catalyst, of rhenium co-promoter selected from sulfur, molybdenum, tungsten, chromium and mixtures thereof supported on a porous refractory support comprising alpha alumina having a surface area ranging from about 0.1 to about 3 $m^2/g$ and a water pore volume ranging from about 0.25 to about 0.55 cc/g wherein the rhenium is applied to the support as ammonium or alkali metal perrhenate or rhenium heptoxide or mixtures thereof and the rhenium co-promoter is applied to the support in the form of an oxidic compound or an oxyanion; the combination of silver, cesium promoter, rhenium, rhenium co-promoter and support affording a higher selectivity to ethylene oxide at a given oxygen conversion level than is obtained under the same reaction conditions with the same combination of silver and support and none, one or two of the promoters selected from cesium, rhenium and rhenium co-promoter.

78. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter, from about 0.2 to about 5 millimoles of rhenium, measured as the metal, per kilogram of total catalyst in a form which is extractable in a dilute (20 millimolar) aqueous solution of sodium hydroxide and from about 0.2 to about 5 millimoles, measured as the element, per kilogram of total catalyst, of a rhenium co-promoter selected from sulfur, molybdenum, tungsten, chromium and mixtures thereof supported on a porous, refractory support comprising alpha alumina having a surface area ranging from about 0.1 to about 3 $m^2/g$ and a water pore volume ranging from about 0.25 to about 0.55 cc/gm; the combination of silver, cesium, rhenium, rhenium co-promoter and support affording a higher selectivity to ethylene oxide at a given oxygen conversion level than is obtained under the same reaction conditions with the same combination of silver and support and none, one or two of the promoters selected from cesium, rhenium and rhenium co-promoter.

79. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter, from about 0.2 to about 5 millimoles of rhenium, measured as the metal, per kilogram of total catalyst in a form which is extractable in a dilute (20 millimolar aqueous solution of sodium hydroxide and from about 0.2 to about 5 millimoles measured as the element, per kilogram of total catalyst, of a rhenium co-promoter selected from sulfur, molybdenum, tungsten, chromium and mixtures thereof supported on a porous refractory support comprising alpha alumina having a surface area ranging from about 01. to about 3 $m^2/g$ and a water pore volume ranging from about 0.25 to about 0.55 cc/g wherein the rhenium is applied to the support as ammonium or alkali metal perrhenate or rhenium heptoxide or mixtures thereof and the rhenium co-promoter is applied to the support as a sulfate, sulfite, suilfonate, molybdate, tungstate, chromate and mixtures thereof; the combination of silver, cesium promoter, rhenium, rhenium co-promoter and support affording a higher selectivity to ethylene oxide at a given oxygen conversion level than is obtained under the same reaction conditions with the same combination of silver and support and none, one or two of the promoters selected from cesium, rhenium and rhenium co-promoter.

80. The process of claim 75 wherein in the catalyst the silver ranges from about 1 to about 25 percent by weight of the total catalyst, the cesium ranges from about 20 to about 1500 parts by weight, measured as the metal, per million parts by weight of the total catalyst, the rhenium ranges from about 0.2 to about 5 millimoles of rhenium measured as the metal, per kilogram of total catalyst and the rhenium co-promoter ranges from about 0.2 to about 5 millimoles, measured as the element, per kilogram of total catalyst.

81. The process of claim 80 wherein in the catalyst the cesium ranges from about 50 to about 1000 ppm by weight of the total catalyst.

82. The process of claim 81 wherein in the catalyst the support has a surface area ranging from about 0.05 to about 5 $m^2/g$.

83. The process of claim 82 wherein in the catalyst the support surface area ranges from about 0.1 to about 3 $m^2/g$.

84. The process of claim 75 wherein in the catalyst said promoting amount of cesium, rhenium and rhenium co-promoter in combination with the silver and support is such as to provide a higher selectivity to ethylene oxide at a given oxygen conversion level than is obtained under the same reaction conditions with the same combination of silver and support and none, one or two of the promoters selected from cesium, rhenium and rhenium co-promoter.

85. The process of claims 76, 77, 78, 79 and 84 wherein in the catalyst the selectivity is measured at an oxygen conversion level of about 40% at a gas hourly space velocity of about 3300 and when the catalyst has been placed onstream for about 16±4 hours.

86. The process of claim 77 wherein in the catalyst the rhenium co-promoter which is applied to the support is selected from sulfate, sulfite, sulfonate, molybdate, tungstate, chromate and mixtures thereof.

87. The process of claims 75, 76, 77, 78 or 79 wherein in the catalyst the cesium, rhenium and rhenium co-prompter are found on the surface of the support or on the surface of the catalyst.

88. The process of claims 75, 76, 77, 78 or 79 wherein in the catalyst the cesium, rhenium and rhenium co-promoter are found individually or in any mixture thereof on the catalyst, on the support, or on both the catalyst and the support.

89. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst prepared by a process which comprises impregnating a porous refractory support with a catalytically effective amount of silver, a promoting amount of alkali metal, a promoting amount of rhenium and a promoting amount of a rhenium co-promoter selected from sulfur, molybdenum, tungsten, chromium and mixtures thereof.

90. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support with one or more solutions comprising silver, alkali metal, rhenium and/or a rhenium co-promoter selected from sulfur, molybdenum, tungsten, chromium and mixtures thereof wherein the concentration of the silver (measured as the metal) in the solution ranges from about 1 g/l to the solubility limit of silver in the solution, the concentration of alkali metal (measured as the metal) in the solution ranges from about $1 \times 10^{-3}$ g/l to about 12 g/l, the concentration of the rhenium (measured as the metal) ranges from about $5 \times 10^{-3}$ g/l to about 20 g/l and the concentration of rhenium co-promoter (measured as the element) ranges from about $1 \times 10^{-3}$ g/l to about 20 g/l to provide the catalyst with a catalytically effective amount of silver, a promoting amount of alkali metal, a promoting amount of rhenium, and a promoting amount of rhenium co-promoter.

91. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support with one or more solutions comprising solvent having silver compound(s) dissolved therein, and/or alkali metal compound(s) dissolved therein and/or rhenium-containing compound(s) dissolved therein and/or rhenium co-promoter compound(s) selected from compound(s) of sulfur, molybdenum, tungsten, chromium and mixtures thereof dissolved therein sufficient to deposit on the support from about 1 to about 25 percent by weight of total catalyst of silver compound(s), measured as the metal, from about 20 to about 1500 ppm by weight of alkali metal compound(s), measured as the metal, from about 0.2 to about 5 millimoles per kilogram of total catalyst, measured as the metal, of rhenium-containing compound(s) and from about 0.2 to about 5 millimoles per kilogram of total catalyst, measured as the element, of rhenium co-promoter compound(s) to provide the catalyst with a catalytically effective amount of silver, a promoting amount of alkali metal, a promoting amount of rhenium and a promoting amount of rhenium co-promoter.

92. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support with one or more solutions comprising silver ions, alkali metal ions, rhenium-containing ions, rhenium co-promoter ions selected from ions containing sulfur, molybdenum, tungsten, chromium and mixtures thereof or mixtures of any of the aforementioned ions thereof sufficient to deposit on the carrier from about 1 to about 25 percent by weight of total catalyst of silver, from about 20 to about 1500 parts by weight, measured as the metal, per million parts by weight of total catalyst, of alkali metal compound(s), from about 0.2 to about 5 millimoles of rhenium-containing compound(s), measured as the metal, per kilogram of total catalyst, and from about 0.2 to about 5 millimoles, measured as the element, per kilogram of total catalyst of rhenium co-promoter compound(s) selected from compound(s) of sulfur, molybdenum, tungsten, chromium and mixtures thereof; and after impregnation, reducing the silver on the support to metallic silver to cause the combination of silver, alkali metal promoter, rhenium, rhenium co-promoter and support to have a higher selectivity to ethylene oxide at a given oxygen conversion level than is obtained under the same reaction conditions with the same combination of silver and support and none, one or two of the promoters selected from alkali metal, rhenium and rhenium co-promoter.

93. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support with one or more solutions comprising silver ions, alkali metal ions, rhenium-containing ions, rhenium co-promoter ions containing sulfur, molybdenum, tungsten, chromium and mixtures thereof or mixtures of any of the aforementioned ions thereof sufficient to deposit on the support from about 1 to about 25 percent by weight of total catalyst of silver, from about 20 to about 1500 parts by weight, measured as the metal, per million parts by weight of total catalyst, of alkali metal compound(s), from about 0.2 to about 5 milimoles of rhenium compound(s), measured as the metal, per kilogram of total catalyst, said rhenium compound(s) providing in the final catalyst rhenium in a form which is extractable in a dilute (20 millimolar) aqueous sodium hydroxide solution and from about 0.2 to about 5 millimoles, measured as the element, per kilogram of total catalyst, of rhenium co-promoter compound(s) selected from compound(s) containing sulfur, molybdenum, tungsten, chromium and mixtures thereof; and after impregnation, reducing the silver on the support to metallic silver to cause the combination of silver, alkali metal promoter, rhenium, rhenium co-promoter and support to have a higher selectivity to ethylene oxide at a given oxygen conversion level than is obtained under the same reaction conditions with the same combination of silver and support and none, one or two of the promoters selected from alkali metal, rhenium and rhenium co-promoter.

94. In a process for the production of ethylene oxide wherein ethylene is contacted in the vapor phase with an oxygen-containing gas at ethylene oxide forming conditions at a temperature ranging between about 180° C. to 330° C. in the presence of a silver metal-containing catalyst, the improvement which comprises using a catalyst prepared by a process which comprises impregnating a porous refractory support comprising alpha alumina with a catalytically effective amount of silver, a promoting amount of higher alkali metal comprising potassium, rubidium, cesium or mixtures thereof, a promoting amount of rhenium and a promoting amount of rhenium co-promoter comprising sulfur, molybdenum, tungsten, chromium and mixtures thereof.

95. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising silver, higher alkali metal selected from the group consisting of potassium, rubidium, cesium and mixtures thereof, rhenium and/or rhenium co-promoter selected from the group consisting of sulfur, molybdenum, tungsten, chromium and mixtures thereof wherein the concentration of the silver (measured as the metal) in the solution ranges from about 1 g/l to the solubility limit of silver in the solution, the concentration of alkali metal (measured as the metal) in the solution ranges from about $1 \times 10^{-3}$ to about 12 g/l, the concentration of the rhenium (measured as the metal) ranges from about $5 \times 10^{-3}$ g/l to about 20 g/l and the concentration of rhenium co-promoter (measured as the element) ranges from about $1 \times 10^{-3}$ g/l to about 20 g/l to provide the catalyst with a catalytically effective amount of silver, a promoting amount of higher alkali metal, a promoting amount of rhenium and a promoting amount of rhenium co-promoter.

96. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising solvent having silver compound(s) dissolved therein, and/or higher alkali metal compound(s) selected from compound(s) of potassium, rubidium, cesium and mixtures thereof dissolved therein and/or rhenium-containing compound(s) dissolved therein and/or rhenium co-promoter compound(s) selected from compound(s) of sulfur, molybdenum, tungsten, chromium and mixtures thereof dissolved therein sufficient to deposit on the support from about 1 to about 25 percent by weight of total catalyst of silver compound(s), measured as the metal, from about 20 to about 1500 ppm by weight of higher alkali metal compound(s), measured as the metal, from about 0.2 to about 5 millimoles per kilogram of total catalyst of rhenium-containing compound(s), measured as the metal and from about 0.2 to about 5 millimoles per kilogram of total catalyst, measured as the element, of rhenium co-promoter compound(s) to provide a catalyst with a catalytically effective amount of silver, a promoting amount of higher alkali metal, a promoting amount of rhenium and a promoting amount of rhenium co-promoter.

97. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support comprising alpha alumina with one or more solutions comprising silver ions, higher alkali metal ions selected from the group consisting of ions of potassium, rubidium, cesium and mixtures thereof, rhenium-containing ions, rhenium co-promoter ions selected from ions containing sulfur, molybdenum, tungsten, chromium and mixtures thereof or mixtures of any of the aforementioned ions thereof sufficient to deposit on the support from about 1 to about 25 percent by weight of total catalyst of silver, from about 20 to about 1500 parts by weight, measured as the metal, per million parts by weight of total catalyst, of higher alkali metal compound(s) selected from compound(s) of potassium, rubidium, cesium and mixtures thereof, from about 0.2 to about 5 millimoles of rhenium-containing compound(s), measured as the metal, per kilogram of total catalyst, and from about 0.2 to about 5 millimoles, measured as the element, per kilogram of total catalyst of rhenium co-promoter compound(s) selected from compound(s) of sulfur, molybdenum, tungsten, chromium and mixtures thereof and after impregnation, reducing the silver on the support to metallic silver to cause the combination of silver, higher alkali metal promoter, rhenium, rhenium co-promoter and support to have a higher selectivity to ethylene oxide at a given oxygen conversion level than is obtained under the same reaction conditions with the same combination of silver and support and none, one or two of the promoters selected from higher alkali metal, rhenium and rhenium co-promoter.

98. In a process for the production of ethylene oxide wherein ethylene is contacted in the vapor phase with an oxygen-containing gas at ethylene oxide forming conditions at a temperature ranging between about 180° C. to 330° C. in the presence of a fixed bed of silver metal-containing catalyst, the improvement which comprises using a catalyst prepared by a process which comprises impregnating a porous, refractory support comprising alpha alumina with one or more solutions comprising silver ions, higher alkali metal ions selected from the group consisting of ions of potassium, rubidium, cesium and mixtures thereof, rhenium-containing ions, rhenium co-promoter ions containing sulfur, molybdenum, tungsten, chromium and mixtures thereof or mixtures of any of the aforementioned ions thereof sufficient to deposit on the support from about 1 to about 25 percent by weight of total catalyst of silver, from about 20 to about 1500 parts by weight, measured as the metal, per million parts by weight of total catalyst, of higher alkali metal compound(s) selected from compound(s) of potassium, rubidium, cesium and mixtures thereof, from about 0.2 to about 5 millimoles of rhenium-containing compound(s), measured as the metal, per kilogram of total catalyst, and from about 0.2 to about 5 millimoles, measured as the element, per kilogram of total catalyst of rhenium co-promoter compound(s) selected from compound(s) of sulfur, molybdenum, tungsten, chromium and mixtures thereof and after impregnation, reducing the silver on the support to metallic silver to cause the combination of silver, higher alkali metal promoter, rhenium, rhenium co-promoter and support to have a higher selectivity to ethylene oxide at a given oxygen conversion level than is obtained under the same reaction conditions with the same combination of silver and support and none, one or two of the promoters selected from higher alkali metal, rhenium and rhenium co-promoter.

99. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst prepared by a process which comprises impregnating a porous refractory support comprising alpha alumina with a catalytically effective amount of silver, a promoting amount of cesium, a promoting amount of rhenium and a promoting amount of rhenium co-promoter comprising sulfur, molybdenum, tungsten, chromium or mixtures thereof.

100. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising silver, cesium, rhenium and/or rhenium co-promoter selected from the group consisting of sulfur, molybdenum, tungsten, chromium and mixtures thereof wherein the concentration of the silver (measured as the metal) in the solution ranges from about 1 g/l to the solubility limit of silver in the solution, the concentration of cesium (measured as the metal) in the solution ranges from about $1 \times 10^{-3}$ g/l to about 12 g/l, the concentration of the rhenium (measured as the metal) ranges from about $5 \times 10^{-3}$ g/l to about 20 g/l and the concentration of rhenium co-promoter (measured as the element) ranges from about $1 \times 10^{-3}$ g/l to about 20 g/l to provide the catalyst with a catalytically effective amount of silver, a promoting amount of cesium, a promoting amount of rhenium and a promoting amount of rhenium co-promoter.

101. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising solvent having silver compound(s) dissolved therein, cesium compound(s) dissolved therein, rhenium-containing compound(s) dissolved therein and rhenium co-promoter compound(s) selected from compound(s) of sulfur, molybdenum, tungsten, chromium and mixtures thereof dissolved therein sufficient to deposit on the support from about 1 to about 25 percent by weight of total catalyst of the silver compound(s), measured as the metal, from about 20 to about 1500 ppm by weight of cesium compound(s) measured as the metal, from about 0.2 to about 5 millimoles per kilogram of total catalyst of rhenium-containing compound(s), measured as the metal, and from about 0.2 to about 5 millimoles per kilogram of total catalyst, measured as the element, of rhenium co-promoter compound(s) to provide the catalyst with a catalytically effective amount of silver, a promoting amount of cesium, a promoting amount of rhenium and a promoting amount of rhenium co-promoter.

102. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support comprising alpha alumina with one or more solutions comprising silver ions, cesium ions, rhenium-containing ions, rhenium co-promoter ions selected from ions containing sulfur, molybdenum, tungsten, chromium and mixtures thereof or mixtures of any of the aforementioned ions thereof sufficient to deposit on the support from about 1 to about 25 percent by weight of total catalyst of silver, from about 20 to about 1500 parts by weight, measured as the metal per million parts by weight of total catalyst, of cesium, from about 0.2 to about 5 millimoles of rhenium-containing compound(s), measured as the metal, per kilogram of total catalyst, and from about 0.2 to about 5 millimoles, measured as the element, per kilogram of total catalyst of rhenium co-promoter compound(s) selected from compound(s) of sulfur, molybdenum, tungsten, chromium and mixtures thereof and after impregnation, reducing the silver on the support to metallic silver to cause the combination of silver, cesium, rhenium, rhenium co-promoter and support to have a higher selectivity to ethylene oxide at a given oxygen conversion level than is obtained under the same reaction conditions with the same combination of silver and support and none, one or two of the promoters selected from cesium, rhenium and rhenium co-promoter.

103. In a process for the production of ethylene oxide wherein ethylene is contacted in the vapor phase with an oxygen-containing gas at ethylene oxide forming conditions at a temperature ranging between about 180° C. to 330° C. in the presence of a fixed bed of silver metal-containing catalyst, the improvement which comprises using a catalyst prepared by a process which comprises impregnating a porous, refractory support comprising alpha alumina with one or more solutions comprising silver ions, cesium ions, rhenium-containing ions, rhenium co-promoter ions containing sulfur, molybdenum, tungsten, chromium and mixtures thereof or mixtures of any of the aforementioned ions thereof, sufficient to deposit on the support from about 1 to about 25 percent by weight of total catalyst of silver, from about 20 to about 1500 parts by weight, measured as the metal, per million parts by weight of total catalyst, of cesium compound(s), from about 0.2 to about 5 millimoles of a rhenium-containing compound(s), measured as the metal, per kilogram of total catalyst, said rhenium-containing compound(s) providing in the final catalyst rhenium in a form which is extractable in a dilute (20 millimolar) aqueous sodium hydroxide solution and from about 0.2 to about 5 millimoles, measured as the element, per kilogram of total catalyst, of rhenium co-promoter compound(s) containing sulfur, molybdenum, tungsten, chromium and mixtures thereof; and after impregnation, reducing the silver on the support to metallic silver to cause the combination of silver, cesium, rhenium, rhenium co-promoter and support to have a higher selectivity to ethylene oxide at a given oxygen conversion level than is obtained under the same reaction conditions with the same combination of silver and support and none, one or two of the promoters selected from cesium, rhenium and rhenium co-promoter.

104. The process of claims 89, 90, 94, 95, 99 and 100 wherein the process for preparing the catalyst the amount of silver added by impregnation ranges from about 1 to about 25 percent by weight, the amount of alkali metal added by impregnation ranges from about 20 to about 1500 ppm by weight, measured as the metal, the amount of rhenium added by impregnation ranges from about 0.2 to about 5 millimoles of rhenium, measured as the metal, per kilogram of total catalyst and the amount of rhenium co-promoter added by impregnation ranges from about 0.2 to about 5 millimoles, measured as the element, per kilogram of total catalyst.

105. The process of claims 89, 90, 94, 95, 99 or 100 wherein in the process for preparing the catalyst the amount of silver found on the surface of the support ranges from about 1 to about 25 percent by weight, the amount of alkali metal found on the catalyst ranges from about 20 to about 1500 ppm by weight, measured as the metal, the amount of rhenium found on the catalyst ranges from about 0.2 to about 5 millimoles of rhenium measured as the metal, per kilogram of total catalyst and the amount of rhenium co-promoter found on the catalyst ranges from about 0.2 to about 5 millimoles, measured as the element, per kilogram of total catalyst.

106. The process of claims 89, 90, 94, 95, 99 or 100 wherein in the process for preparing the catalyst the amount of silver found on the surface of the support ranges from about 1 to about 25 percent by weight, the amount of alkali metal found on the surface of the support ranges from about 20 to about 1500 ppm by weight, measured as the metal, the amount of rhenium found on the surface of the support ranges from about 0.2 to about 5 millimoles of rhenium, measured as the metal, per kilogram of total catalyst and the amount of rhenium co-promoter found on the surface of the support ranges from about 0.2 to about 5 millimoles, measured as the element, per kilograms of total catalyst.

107. The process of claims 89, 90, 91, 94, 95, 96, 99, 100 or 101 wherein in the process for preparing the catalyst after impregnation the silver is reduced to metallic silver.

108. The process as in any of claim 89–103 wherein in the process for preparing the catalyst after impregnation the silver is reduced to metallic silver by heating at a temperature between about 75° C. to about 400° C.

109. The process as in any of claims 89–103 wherein in the process for preparing the catalyst after impregnation the silver is reduced to metallic silver by heating at a temperature between about 50° C. to about 600° C.

110. The process of claims 90, 91, 92, 93, 95, 96, 97, 98, 100, 101, 102 or 103 wherein in the process for preparing the catalyst the solution containing silver also comprises water and vicinal alkylenediamine(s) of from 2 to 4 carbon atoms.

111. The process of claims 90, 91, 92, 93, 95, 96, 97, 98, 100, 101, 102 or 103 wherein in the process for preparing the catalyst the solution containing silver also comprises water and ethylenediamine.

112. The process of claims 90, 91, 92, 93, 95, 96, 97, 98, 100, 101, 102 or 103 wherein in the process for preparing the catalyst the solution containing silver also comprises water, vicinal alkalenediamine(s) of from 2 to 4 carbon atoms and vicinal alkanolamine(s) of from 2 to 4 carbon atoms.

113. The process of claims 90, 91, 92, 93, 95, 96, 97, 98, 100, 101, 102 or 103 wherein in the process for preparing the catalyst the solution containing silver also comprises water, ethylenediamine and monoethanolamine.

114. The process of claims 91, 96 or 101 wherein in the process for preparing the catalyst the silver compound is selected from silver oxalate, silver oxide, silver carbonate, silver lactate and mixtures thereof.

115. The process of claims 91, 96 or 101 wherein in the process for preparing the catalyst the alkali metal compound is a hydroxide and/or a nitrate.

116. The process of claims 91, 96 or 101 wherein in the process for preparing the catalyst the rhenium-containing compound is ammonium and/or alkali metal perrhenate and/or rhenium heptoxide.

117. The process of claims 91, 96 or 101 wherein in the process for preparing the catalyst the sulfur compound is ammonium or alkali metal sulfate, sulfite or sulfonate or sulfuric, sulfurous or sulfonic acid, the tungsten compound is ammonium or alkali metal tungstate or tungstic acid, the molybdenum compound is ammonium or alkali metal molybdate or molybdic acid and the chromium compound is ammonium or alkali metal chromate or dichromate or chromic or dichromic acid.

118. The process of claims 91, 96 or 101 wherein in the process for preparing the catalyst the alkali metal compound is cesium hydroxide or cesium nitrate, the rhenium compound is ammonium or alkali metal perrhenate or rhenium heptoxide, the sulfur compound is ammonium or alkali metal sulfate, sulfite or sulfonate or sulfuric, sulfurous or sulfonic acid, the tungsten compound is ammonium or alkali metal tungstate or tungstic acid, the molybdenum compound is ammonium or alkali metal molybdate or molybdic acid and the chromium compound is ammonium or alkali metal chromate or dichromate or chromic or dichromic acid.

119. The process of claims 91, 96 or 101 wherein in the process for preparing the catalyst the silver compound is selected from silver oxalate, silver oxide, silver carbonate, silver lactate and mixtures thereof, the alkali metal compound is cesium hydroxide or cesium nitrate, the rhenium compound is ammounium and alkali metal perrhenate or rhenium heptoxide, the sulfur compound is ammonium or alkali metal sulfate, sulfite or sulfonate or sulfuric, sulfurous or sulfonic acid, the tungsten compound is ammonium or alkali metal tungstate or tungstic acid, the molybdenum compound is ammonium or alkali metal molybdate or molybdic acid and the chromium compound is ammonium or alkali metal chromate or dichromate or chromic or dichromic acid.

120. The process of claims 92, 93, 97, 98, 102 or 103 wherein in the process for preparing the catalyst the rhenium-containing ions are perrhenate ions.

121. The process of claims 92, 93, 97, 98, 102 or 103 wherein in the process for preparing the catalyst the rhenium co-promoter ions are selected from sulfate, sulfite, sulfonate, molybdate, tungstate, chromate ions and mixtures thereof.

122. The process of claims 92, 93, 97, 98, 102 or 103 wherein in the process for preparing the catalyst the rhenium-containing ions are perrhenate ions and the rhenium co-promoter ions are selected from sulfate, sulfite, sulfonate, molybdate, tungstate, chromate ions and mixtures thereof.

123. In the process of claims 92, 93, 97, 98, 102 or 103 wherein in the process for preparing the catalyst, the selectivity is measured at an oxygen conversion of about 40% at a gas hourly space velocity of about 330 and when the catalyst has been placed on stream for about 16±4 hours.

124. The process of any one of claims 1–5 or 89–93 wherein in the catalyst or in the process for preparing the catalyst, the alkali metal is cesium plus an alkali metal selected from the group consisting of lithium, sodium, potassium and mixtures thereof.

125. The process of any one of claims 1, 31, 32 or 75 wherein in the catalyst or in the process for preparing the catalyst. The support has a surface area ranging from about 0.05 to about 10 $m^2/g$.

* * * * *